(12) United States Patent
Kamon

(10) Patent No.: US 10,986,980 B2
(45) Date of Patent: Apr. 27, 2021

(54) IMAGE PROCESSING DEVICE, METHOD FOR OPERATING SAME, ENDOSCOPE PROCESSOR DEVICE, AND METHOD FOR OPERATING SAME

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 299 days.

(21) Appl. No.: 16/143,498

(22) Filed: Sep. 27, 2018

(65) Prior Publication Data

US 2019/0021579 A1 Jan. 24, 2019

Related U.S. Application Data

(63) Continuation of application No. PCT/JP2017/006198, filed on Feb. 20, 2017.

(30) Foreign Application Priority Data

Apr. 1, 2016 (JP) .............................. JP2016-074254

(51) Int. Cl.
*A61B 1/00* (2006.01)
*G06T 7/586* (2017.01)
(Continued)

(52) U.S. Cl.
CPC ........ *A61B 1/00009* (2013.01); *A61B 1/0005* (2013.01); *A61B 1/00006* (2013.01);
(Continued)

(58) Field of Classification Search
CPC ... A61B 1/00009; A61B 1/0005; A61B 1/043; A61B 1/0638; A61B 1/0646;
(Continued)

(56) References Cited

U.S. PATENT DOCUMENTS 6,080,104 A * 6/2000 Ozawa ................. H04N 5/2351
348/69
2009/0247881 A1 10/2009 Maeda et al.
(Continued)

FOREIGN PATENT DOCUMENTS

EP 2305094 4/2011
EP 2368486 9/2011
(Continued)

OTHER PUBLICATIONS

Office Action of Japan Counterpart Application, with English translation thereof, dated Sep. 3, 2019, pp. 1-10.
(Continued)

*Primary Examiner* — Eric F Winakur
*Assistant Examiner* — Abid A Mustansir
(74) *Attorney, Agent, or Firm* — JCIPRNET

(57) ABSTRACT

Provided are an image processing device and a method for operating the same, and an endoscope processor device and a method for operating the same that accurately measure the blood vessel depth of blood vessels in an observation target. A data set including a plurality of items of measurement data in which blood vessel index values, such as blood vessel contrast and a plurality of blood vessel index value variation factors including the blood vessel depth are associated with each other is stored in a data set storage unit 97. A specific blood vessel index value variation factor other than the blood vessel depth is measured. The data set is narrowed to a sub-data set having the specific blood vessel index value variation factor. A blood vessel depth corresponding to a blood vessel index value calculated by the blood vessel index value calculation unit is found from the sub-data set.

15 Claims, 17 Drawing Sheets

(51) Int. Cl.
  *A61B 1/06*       (2006.01)
  *A61B 5/00*       (2006.01)
  *A61B 1/04*       (2006.01)
  *A61B 5/103*      (2006.01)
  *A61B 5/107*      (2006.01)
  *A61B 5/1455*     (2006.01)
  *A61B 5/1459*     (2006.01)
  *A61B 1/045*      (2006.01)

(52) U.S. Cl.
  CPC ............ *A61B 1/043* (2013.01); *A61B 1/0638* (2013.01); *A61B 1/0646* (2013.01); *A61B 1/0653* (2013.01); *A61B 5/0084* (2013.01); *A61B 5/1032* (2013.01); *A61B 5/1076* (2013.01); *A61B 5/1079* (2013.01); *A61B 5/1459* (2013.01); *A61B 5/14551* (2013.01); *A61B 5/489* (2013.01); *A61B 5/743* (2013.01); *G06T 7/586* (2017.01); *A61B 1/045* (2013.01); *G06T 2207/10064* (2013.01); *G06T 2207/10068* (2013.01); *G06T 2207/10152* (2013.01); *G06T 2207/30101* (2013.01)

(58) Field of Classification Search
  CPC ... A61B 1/0653; A61B 5/0084; A61B 5/1032; A61B 5/1076; A61B 5/1079; A61B 5/14551; A61B 5/1459; A61B 5/489; A61B 5/743; A61B 1/045; G06T 7/586; G06T 2207/10064; G06T 2207/10068; G06T 2207/10152; G06T 2207/30101
  See application file for complete search history.

(56) References Cited

U.S. PATENT DOCUMENTS

| | | | |
|---|---|---|---|
| 2011/0077462 A1 | 3/2011 | Saitou et al. | |
| 2012/0053434 A1* | 3/2012 | Saito | A61B 1/063 600/324 |
| 2012/0190922 A1* | 7/2012 | Kaku | A61B 1/0005 600/109 |
| 2015/0363932 A1 | 12/2015 | Hirota et al. | |

FOREIGN PATENT DOCUMENTS

| | | |
|---|---|---|
| EP | 2368487 | 9/2011 |
| JP | 2009039515 | 2/2009 |
| JP | 2009254794 | 11/2009 |
| JP | 2011218135 | 11/2011 |
| JP | 2012187139 | 10/2012 |
| JP | 2013144039 | 7/2013 |
| JP | 2013202189 | 10/2013 |
| JP | 2014161627 | 9/2014 |
| JP | 2015042274 | 3/2015 |

OTHER PUBLICATIONS

"Search Report of Europe Counterpart Application", dated Feb. 28, 2019, p. 1-p. 8.

"Written Opinion of the International Searching Authority (Form PCT/ISA/237) of PCT/JP2017/006198," dated May 16, 2017, with English translation thereof, pp. 1-9.

"International Search Report (Form PCT/ISA/210) of PCT/JP2017/006198," dated May 16, 2017, with English translation thereof, pp. 1-4.

* cited by examiner

FIG. 13

| OXYGEN SATURATION | BLOOD VESSEL THICKNESS | BLOOD VESSEL DEPTH | BLOOD VESSEL CONTRAST |
|---|---|---|---|
| 100% | $\phi 1$ | d1 | Ct(100, $\phi 1$, d1) |
| | $\phi 1$ | d2 | Ct(100, $\phi 1$, d2) |
| | ⋮ | ⋮ | ⋮ |
| | $\phi 2$ | d1 | Ct(100, $\phi 2$, d1) |
| | ⋮ | ⋮ | ⋮ |
| | $\phi m$ | d1 | Ct(100, $\phi m$, d1) |
| | ⋮ | ⋮ | ⋮ |
| 99% | $\phi 1$ | d1 | Ct(99, $\phi 1$, d1) |
| | ⋮ | ⋮ | ⋮ |
| ⋮ | ⋮ | ⋮ | ⋮ |
| | ⋮ | ⋮ | ⋮ |
| $s^*$% | $\phi^*$ | $d^*$ | Ct($s^*$, $\phi^*$, $d^*$) |
| | ⋮ | ⋮ | ⋮ |
| ⋮ | ⋮ | ⋮ | ⋮ |
| 0% | ⋮ | ⋮ | ⋮ |

120

IMAGE PROCESSING DEVICE, METHOD FOR OPERATING SAME, ENDOSCOPE PROCESSOR DEVICE, AND METHOD FOR OPERATING SAME

CROSS-REFERENCE TO RELATED APPLICATIONS

This application is a Continuation of PCT International Application No. PCT/JP2017/006198 filed on Feb. 20, 2017, which claims priority under 35 U.S.C § 119(a) to Japanese Patent Application No. 2016-074254 filed on Apr. 1, 2016. Each of the above application(s) is hereby expressly incorporated by reference, in its entirety, into the present application.

BACKGROUND OF THE INVENTION

1. Field of the Invention

The present invention relates to an image processing device and a method for operating the same, and an endoscope processor device and a method for operating the same that measure the blood vessel depth of blood vessels in an observation target.

2. Description of the Related Art

In the medical field, it is general to perform diagnosis using endoscopic systems including a light source device, an endoscope, and a processor device. Additionally, in recent years, not only normal observation using broadband light, such as white light, but also special observation using biological function information, such as oxygen saturation and blood vessel depth, has also been performed.

For example, in JP2013-202189A (JP5774531B), brightness ratios S1/S3 and S2/S3, which are one of index values (blood vessel index values) relating to blood vessels, are calculated on the basis of image signals S1, S2, and S3 obtained by sequentially radiating narrowband lights (central wavelengths of 445 nm, 473 nm, and 405 nm), respectively, oxygen saturation and blood vessel depth are calculated from the brightness ratios S1/S3 and S2/S3, and imaging is performed by color processing of pseudo-colors or the like.

SUMMARY OF THE INVENTION

Regarding the oxygen saturation, the oxygen saturation can be accurately measured by incorporating not only blood vessel index values, such as the brightness ratios S1/S3 and S2/S3 shown in JP2013-202189A (JP5774531B), but also other measurement techniques. Meanwhile, most of methods of calculating the blood vessel depth are performed only using the blood vessel index values. Due to the reasons as shown below, there is a case where the blood vessel depth cannot be accurately measured.

For example, as illustrated in FIGS. 25 and 26, a relationship between blood vessel contrast that is one of the blood vessel index values and the blood vessel depth shows a tendency that, as the blood vessel depth becomes deeper, the blood vessel contrast becomes lower, irrespective of the magnitude of the blood vessel depth or the oxygen saturation. However, as illustrated in FIG. 25, since the relationship between the blood vessel contrast and the blood vessel depth varies in a case where the blood vessel thickness is large and in a case where the blood vessel thickness is small, the blood vessel depth cannot be accurately found only with the blood vessel contrast in a case where the blood vessel thickness changes. Additionally, as illustrated in FIG. 26, since the relationship between the blood vessel contrast and the blood vessel depth varies in a case where the oxygen saturation is low and in a case where the oxygen saturation is high, the blood vessel depth cannot be accurately found only with the blood vessel contrast in a case where the oxygen saturation changes. Hence, techniques capable of accurately measuring the blood vessel depth of blood vessels in an observation target using not only the blood vessel index values, such as the brightness ratios and the blood vessel contrast but also other information and measurement techniques have been required.

An object of the invention is to provide to an image processing device and a method for operating the same, and an endoscope processor device and a method for operating the same that accurately measure the blood vessel depth of blood vessels in an observation target, using not only blood vessel index values but also other information.

An image processing device of the aspect of the invention is an image processing device that measures a blood vessel depth of a blood vessel in an observation target. The image processing device comprises an image acquisition unit that acquires an image obtained by imaging the observation target; a blood vessel index value calculation unit that calculates a blood vessel index value from a blood vessel index value image in the image; a data set storage unit that stores a data set including a plurality of items of measurement data in which the blood vessel index value and a plurality of blood vessel index value variation factors that vary the blood vessel index value and include the blood vessel depth are associated with each other; a blood vessel index value variation factor measurement unit that measures a specific blood vessel index value variation factor other than the blood vessel depth among the plurality of blood vessel index value variation factors; and a blood vessel depth calculation unit that narrows the data set to a sub-data set having the specific blood vessel index value variation factor and calculates a blood vessel depth corresponding to the blood vessel index value calculated by the blood vessel index value calculation unit from the sub-data set.

It is preferable that the image processing device further comprises a measurement target blood vessel designation unit that designates a measurement target blood vessel to be a measurement target for the blood vessel depth in the observation target, and the blood vessel index value calculation unit calculates the blood vessel index value of the measurement target blood vessel. It is preferable that the blood vessel index value image includes multiple-wavelength images, and the blood vessel index value calculation unit calculates the blood vessel index value of the measurement target blood vessel on the basis of the multiple-wavelength images. It is preferable that the blood vessel index value calculation unit calculates the blood vessel index value for each of the multiple-wavelength images, and calculates the blood vessel index value of the measurement target blood vessel by weighting the calculated blood vessel index values respectively and adding the calculated blood vessel index values to each other, and weighting coefficients of the blood vessel index values are set on the basis of wavelength components of the images used for the calculation of the blood vessel index values. It is preferable that the image processing device further comprises a blood vessel index value variation factor selection unit that selects a specific blood vessel index value variation factor measured in the blood vessel index value variation factor measurement unit from the plurality of blood vessel index value variation factors.

It is preferable that the image processing device further comprises a blood vessel depth measurement image generation unit that generates a blood vessel depth measurement image for displaying a calculation result of the blood vessel depth calculation unit on a display unit. It is preferable that the blood vessel index value is a value obtained by combining at least two or more of a blood vessel contrast, a brightness value of a blood vessel part, or color information of the blood vessel part together. It is preferable that the blood vessel index value variation factors are values obtained by combining two or more of a blood vessel thickness, an oxygen saturation, a blood vessel density, an imaging distance, an imaging angle, a yellow coloring agent density, or a scattering coefficient of a mucous membrane together.

It is preferable that the specific blood vessel index value variation factors are a blood vessel thickness and an oxygen saturation, and the blood vessel index value variation factor measurement unit has a blood vessel thickness measurement unit that measures the blood vessel thickness, and an oxygen saturation measurement unit that measures the oxygen saturation. It is preferable that the blood vessel index value is a blood vessel contrast, and the data set storage unit stores a data set including measurement data in which the blood vessel contrast, the oxygen saturation, the blood vessel depth, and the blood vessel depth are associated with each other.

The invention is an endoscope processor device that measures a blood vessel depth of a blood vessel in an observation target. The endoscope processor device comprises an image acquisition unit that acquires an image obtained by imaging the observation target; a blood vessel index value calculation unit that calculates a blood vessel index value from a blood vessel index value image in the image; a data set storage unit that stores a data set including a plurality of items of measurement data in which the blood vessel index value and a plurality of blood vessel index value variation factors that vary the blood vessel index value and include the blood vessel depth are associated with each other; a blood vessel index value variation factor measurement unit that measures a specific blood vessel index value variation factor other than the blood vessel depth among the plurality of blood vessel index value variation factors; and a blood vessel depth calculation unit that narrows the data set to a sub-data set having the specific blood vessel index value variation factor and calculates a blood vessel depth corresponding to the blood vessel index value calculated by the blood vessel index value calculation unit from the sub-data set.

The aspect of the invention is a method for operating an image processing device that measures a blood vessel depth of a blood vessel in an observation target. The method comprises a step of acquiring an image obtained by imaging the observation target, by an image acquisition unit; a step of calculating a blood vessel index value from a blood vessel index value image in the image, by a blood vessel index value calculation unit; a step of measuring a specific blood vessel index value variation factor other than the blood vessel depth among a plurality of blood vessel index value variation factors that vary the blood vessel index value and include the blood vessel depth, by a blood vessel index value variation factor measurement unit; and a step of narrowing a data set including a plurality of items of measurement data in which the blood vessel index value and a plurality of blood vessel index value variation factors are associated with each other to a sub-data set having the specific blood vessel index value variation factor and calculating a blood vessel depth corresponding to the blood vessel index value calculated by the blood vessel index value calculation unit from the sub-data set, by a blood vessel depth calculation unit.

The aspect of the invention is a method for operating an endoscope processor device that measures a blood vessel depth of a blood vessel in an observation target. The method comprises a step of acquiring an image obtained by imaging the observation target, by an image acquisition unit; a step of calculating a blood vessel index value from a blood vessel index value image in the image, by a blood vessel index value calculation unit; a step of measuring a specific blood vessel index value variation factor other than the blood vessel depth among a plurality of blood vessel index value variation factors that vary the blood vessel index value and include the blood vessel depth, by a blood vessel index value variation factor measurement unit; and a step of narrowing a data set including a plurality of items of measurement data in which the blood vessel index value and a plurality of blood vessel index value variation factors are associated with each other to a sub-data set having the specific blood vessel index value variation factor and calculating a blood vessel depth corresponding to the blood vessel index value calculated by the blood vessel index value calculation unit from the sub-data set, by a blood vessel depth calculation unit.

According to the invention, the blood vessel depth of the blood vessel in the observation target can be accurately measured by using not only the blood vessel index values but also other information.

BRIEF DESCRIPTION OF THE DRAWINGS

FIG. 13 is an illustrative view illustrating a data set.

DESCRIPTION OF THE PREFERRED EMBODIMENTS

First Embodiment

Figure 1:
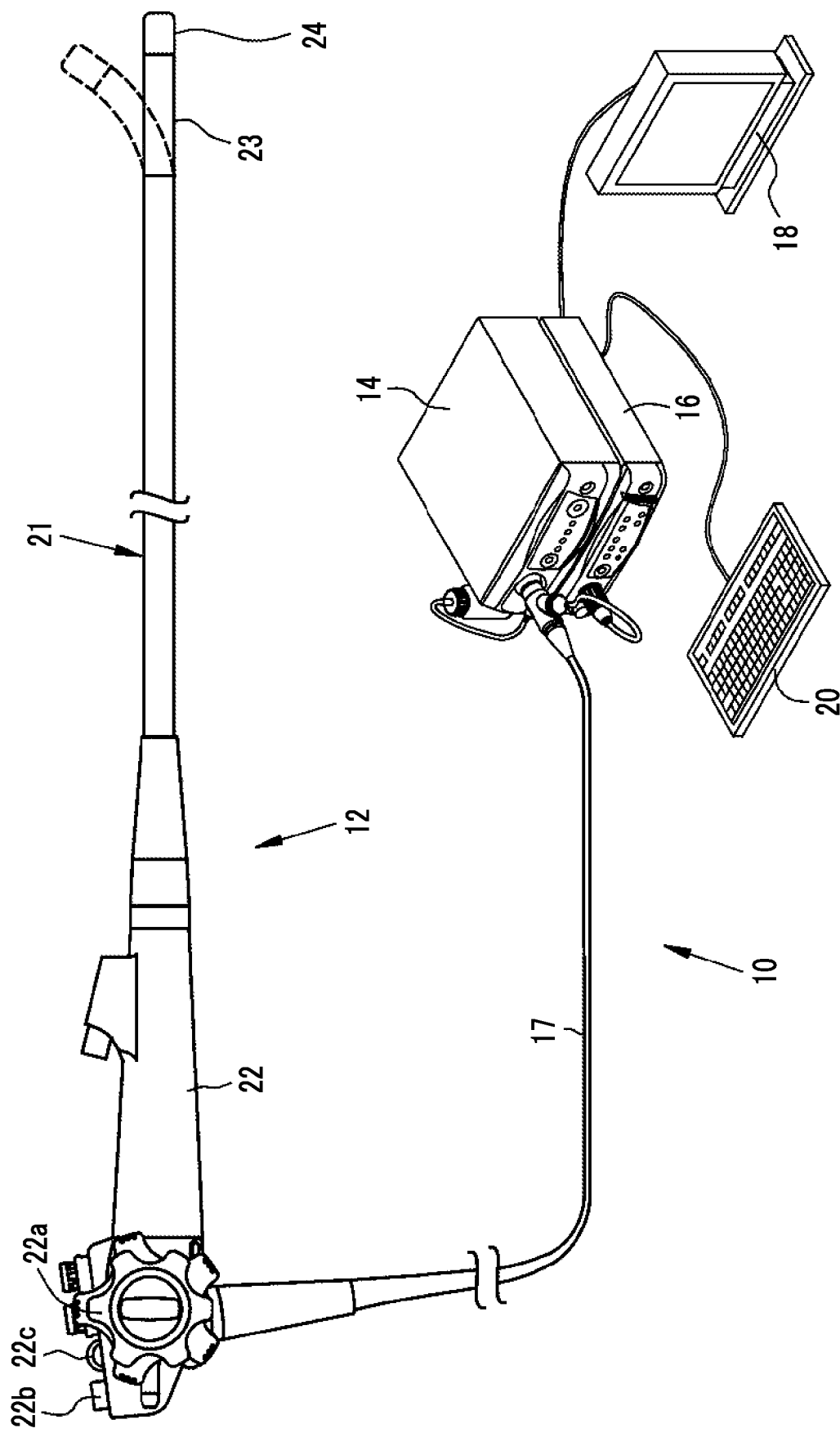
FIG. 1 is an external view of an endoscopic system.

As illustrated in FIG. 1, an endoscopic system 10 of a first embodiment has an endoscope 12, a light source device 14, a processor device 16 (corresponding to an "image processing device" and an "endoscope processor device" of the embodiment of the invention), a monitor 18 (corresponding to a display unit of the embodiment of the invention), and a console 20. The endoscope 12 is optically connected to the light source device 14 and is electrically connected to the processor device 16. The endoscope 12 has an insertion part 21 to be inserted into a subject, an operating part 22 provided at a proximal end portion of the insertion part 21, and a bending part 23 and a distal end part 24 provided on a distal end side of the insertion part 21. By operating an angle knob 22a of the operating part 22, the bending part 23 makes a bending motion. The distal end part 24 can be directed to a desired direction along with this bending motion.

Additionally, the operating part 22 is provided with an observation mode changeover SW 22b, a zooming operation part 22c, a freezing button (not illustrated) for saving a still image in addition to the angle knob 22a. The mode changeover SW 22b is used for a switching operation among four types of modes, such as a normal observation mode, an oxygen saturation mode, a blood vessel thickness measurement mode, and a blood vessel depth measurement mode.

The normal observation mode is a mode in which a normal optical image obtained by imaging an observation target within a subject in full colors is displayed on the monitor 18. The oxygen saturation mode is a mode in which an oxygen saturation image obtained by imaging the oxygen saturation of hemoglobin into blood of the observation target is displayed on the monitor 18. The blood vessel thickness measurement mode is a mode in which the thickness of a blood vessel of the observation target is measured and a measurement result is displayed on the monitor 18. The Blood vessel depth measurement mode is a mode in which the depth of a blood vessel of the observation target is measured and a measurement result is displayed on the monitor 18. The zooming operation part 22c is used for a zooming operation of driving a zoom lens 47 (refer to FIG. 2) within the endoscope 12 to magnify the observation target.

The processor device 16 is electrically connected to the monitor 18 and the console 20. The monitor 18 displays images, such as the normal optical image and the oxygen saturation image, and information (hereinafter referred to as image information and the like) on these images. The console 20 functions as a user interface (UI) that receives input operations, such as a function setting. In addition, a recording unit (not illustrated) that records the image information and the like may be connected to the processor device 16.

Figure 2:
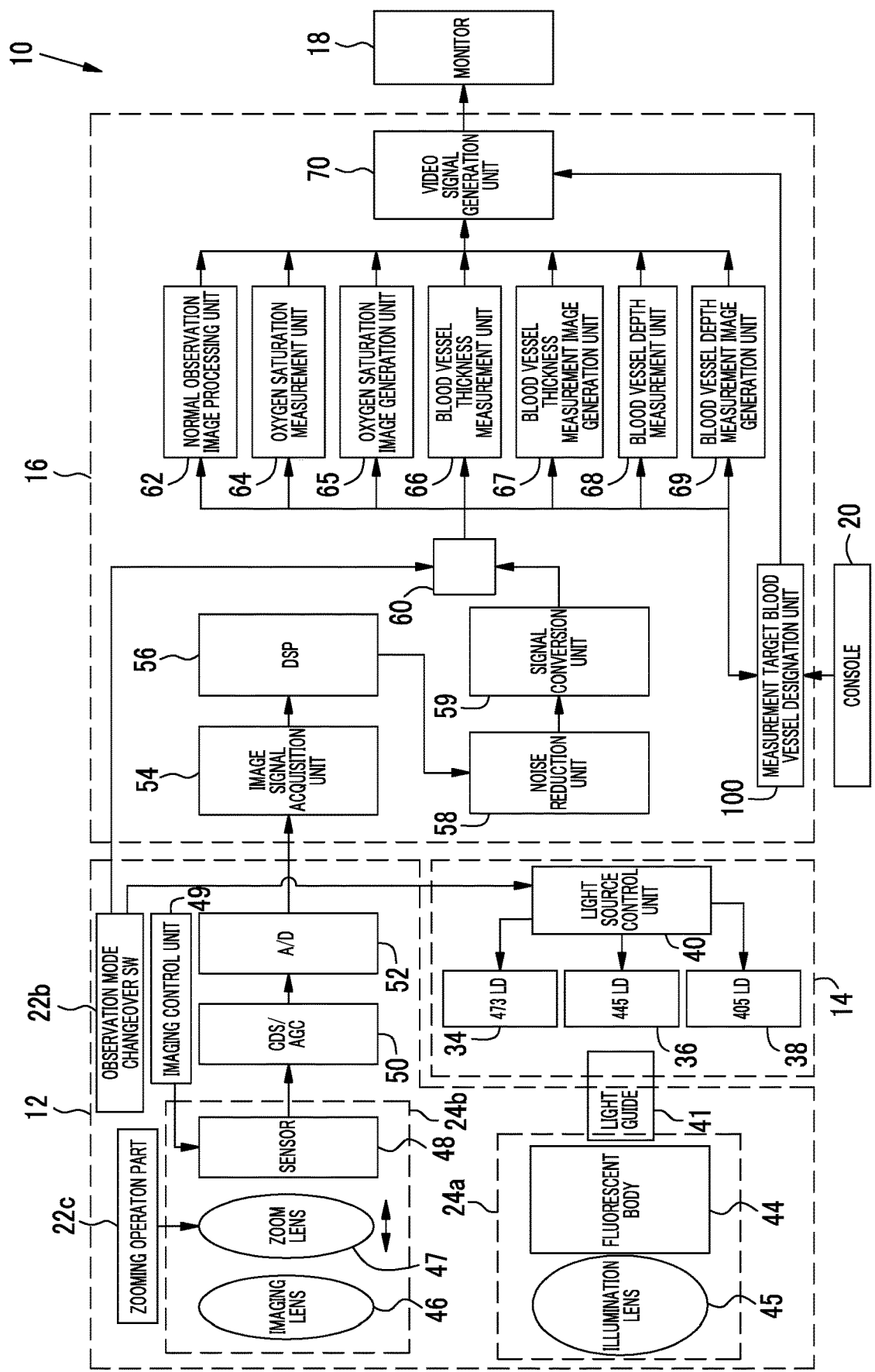
FIG. 2 is a block diagram of an endoscopic system of a first embodiment.

As illustrated in FIG. 2, the light source device 14 includes a first blue laser light source (473LD (Laser Diode) 34 that emits first blue laser light having a central wavelength of 473 nm, a second blue laser light source (445LD) 36 that emits second blue laser light having a central wavelength of 445 nm, and a violet laser light source (405LD) 38 that emits violet laser light having a central wavelength 405 nm as light emission sources. The light emission amounts and the light emission timings of the respective light sources 34, 36, and 38 including these semiconductor light emitting elements are individually controlled by a light source control unit 40.

In addition, it is preferable that the half-widths of the first and second blue laser lights and the violet laser light, are about ±10 nm. Additionally, it is preferable that the central wavelengths of the first and second blue laser lights and the violet laser light fall within a range of ±5 to 10 nm with respect to the above central wavelengths shown above. Additionally, the central wavelengths of the first and second blue laser lights and the violet laser light may be the same as or different from peak wavelengths. As the first blue laser light source 34, the second blue laser light source 36, and the violet laser light source 38, broad area type InGaN-based laser diodes can be utilized, and InGaNAs-based laser diodes and GaNAsb-based laser diodes can also be used. Additionally a configuration formed of a light emitter, such as a light emitting diode, may be adopted as the above light source.

The light source control unit 40 performs the control of turning on only the second blue laser light source 36 in the case of the normal observation mode and the blood vessel thickness measurement mode. Additionally, in the case of the oxygen saturation mode and the blood vessel depth measurement mode, the light source control unit 40 performs the control of alternately turning on the first blue laser light source 34 and the second blue laser light source 36 at one-frame intervals. In addition, in any mode of the normal observation mode, the oxygen saturation mode, the blood vessel thickness measurement mode, and the blood vessel depth measurement mode, the control of turning on the violet laser light source 38 simultaneously may also be performed in a case where the second blue laser light source 36 is turned on.

The first and second blue laser lights and the violet laser light, which are emitted from the respective light sources 34, 36, and 38, enter a light guide 41 via optical members (neither is illustrated), such as a condensing lens, an optical fiber, and a multiplexer. The light guide 41 is built in a universal cord 17 (refer to FIG. 1) that connects the light source device 14 and the endoscope 12 to each other, and the endoscope 12. The light guide 41 propagates the first and second blue laser lights and the violet laser light from the respective light sources 34, 36, and 38 to the distal end part 24 of the endoscope 12. In addition, a multimode fiber can be used as the light guide 41. As an example, a fine-diameter fiber cable of which the core diameter is 105 μm, the clad diameter is 125 μm, and a diameter including a protective layer used as an outer cover is φ0.3 mm to 0.5 mm can be used.

The distal end part 24 of the endoscope 12 has an illumination optical system 24a and an imaging optical system 24b. The illumination optical system 24a is provided with a fluorescent body 44 and an illumination lens 45. The first and second blue laser lights and the violet laser light enter the fluorescent body 44 from the light guide 41. The fluorescent body 44 emits fluorescence by radiating the first or second blue laser light. Additionally, a portion of the first or second blue laser light is transmitted through the fluorescent body 44 as it is. In contrast, substantially all of the violet laser light is transmitted through the fluorescent body 44. The light emitted from the fluorescent body 44 is radiated to the observation target via the illumination lens 45.

Figure 3:
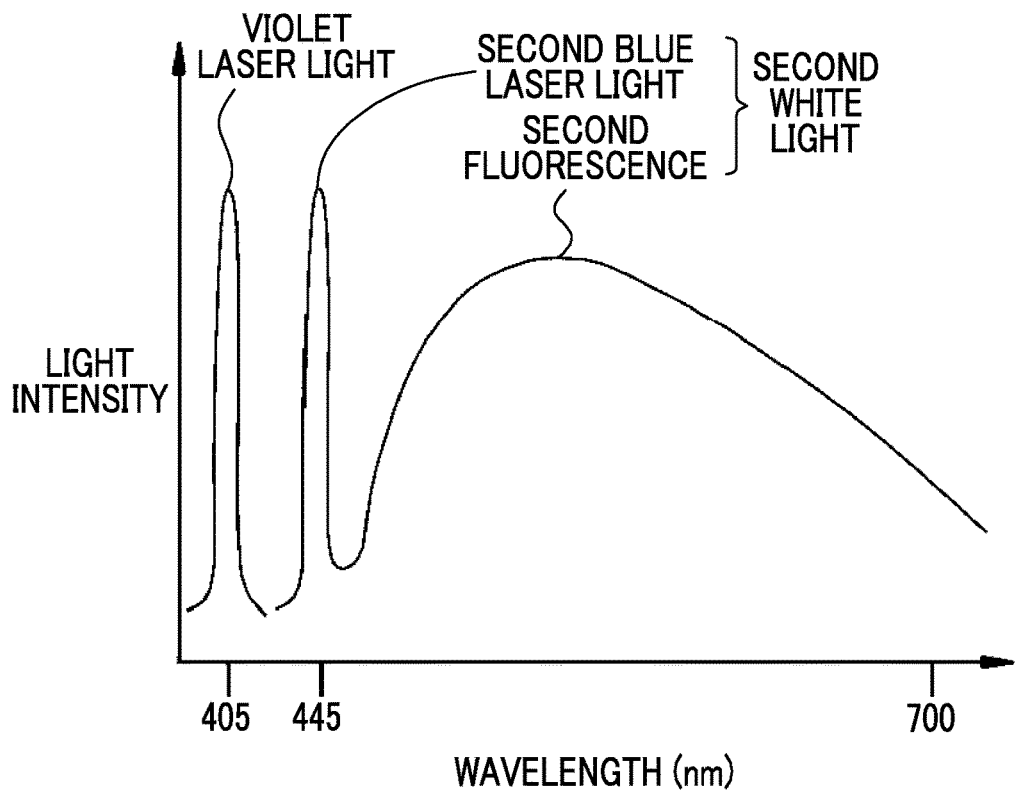
FIG. 3 is a graph illustrating spectra of second white light and blue laser light.

The spectrum and the light emission timing of the light radiated to the observation target vary in every mode. In the normal observation mode and the blood vessel thickness measurement mode, only the second blue laser light enters the fluorescent body 44. Therefore, as illustrated in FIG. 3, second white light including the second blue laser light, and green to red second fluorescence excited and emitted from the fluorescent body 44 due to the second blue laser light, is radiated to the observation target. In addition, in a case where the violet laser light is emitted simultaneously with the second blue laser light, the violet laser light is transmitted as it is without being absorbed by the fluorescent body 44. Therefore, fluorescence is hardly emitted by the violet laser light.

Figure 4:
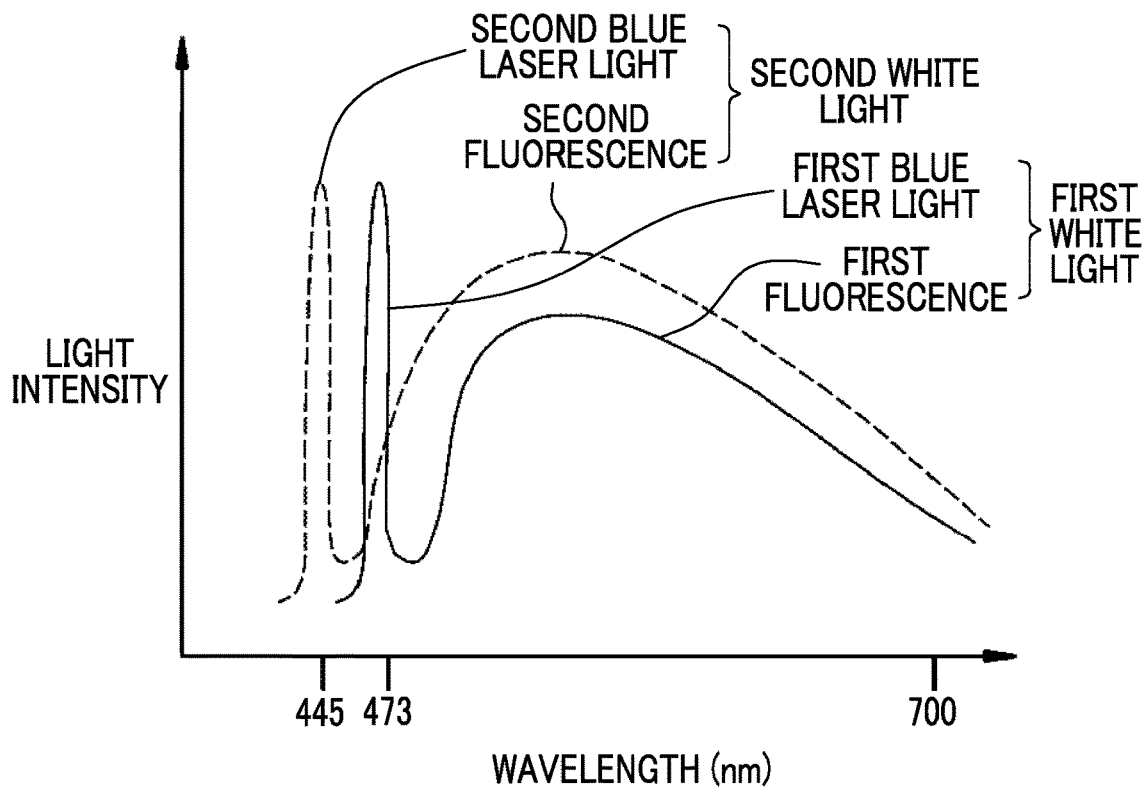
FIG. 4 is a graph illustrating the spectrum of first white light.

In the oxygen saturation mode and the blood vessel depth mode, as the first blue laser light and the second blue laser light alternately enter the fluorescent body 44, as illustrated in FIG. 4, first white light including the first blue laser light, and green to red first fluorescence excited and emitted from the fluorescent body 44 due to the first blue laser light, and the second white light are alternately radiated to the observation target. The first fluorescence and the second fluorescence have substantially the same waveform (spectrum shape). However, in the fluorescent body 44, since an absorption amount for the second blue laser light is larger than an absorption amount for the first blue laser light, the intensity of the whole wavelength of the second fluorescence is larger than the intensity of the first fluorescence in a case where the first and second blue laser lights having the same intensity enter the fluorescent body 44.

In addition, as the fluorescent body 44, it is preferable to use those configured to include a plurality of items of fluorescent bodies (for example, a YAG-based fluorescent body or fluorescent bodies, such as BAM (BaMgAl10O17)) that absorb portions of the first and second blue laser lights and are excited to emit light in green to red. Additionally, as in the present embodiment, in a case where a semiconductor light emitting element is used as an excitation light source of the fluorescent body 44, the first white light and the second white light having higher intensity are obtained with high light emission efficiency. Additionally, the intensity of each white light can be easily adjusted, and changes in color temperature and chromaticity can be suppressed to be small.

The imaging optical system 24b of the endoscope 12 has an imaging lens 46, the zoom lens 47, and a sensor 48 (refer to FIG. 2). The reflected light from the observation target enters the sensor 48 via the imaging lens 46 and the zoom lens 47. Accordingly, a reflected image of the observation target is formed on the sensor 48. The zoom lens 47 is moved by operating the zooming operation part 22c between a telephoto end and a wide end.

The sensor 48 is a color image pickup element, and captures the reflected image of the observation target to output image signals. As the sensor 48, for example, a charge coupled device (CCD) type image sensor or a complementary metal oxide semiconductor (CMOS) image sensor can be used. In the present embodiment, the sensor 48 is the CCD image sensor. Additionally, the sensor 48 includes an R pixel provided with an R color filter, a G pixel provided with a G color filter, and a B pixel (blue pixel) provided with a B color filter, with respect to an imaging surface. Image signals in three colors of R, and B are output by performing photoelectric conversion with pixels in the respective colors of RGB.

Figure 5:
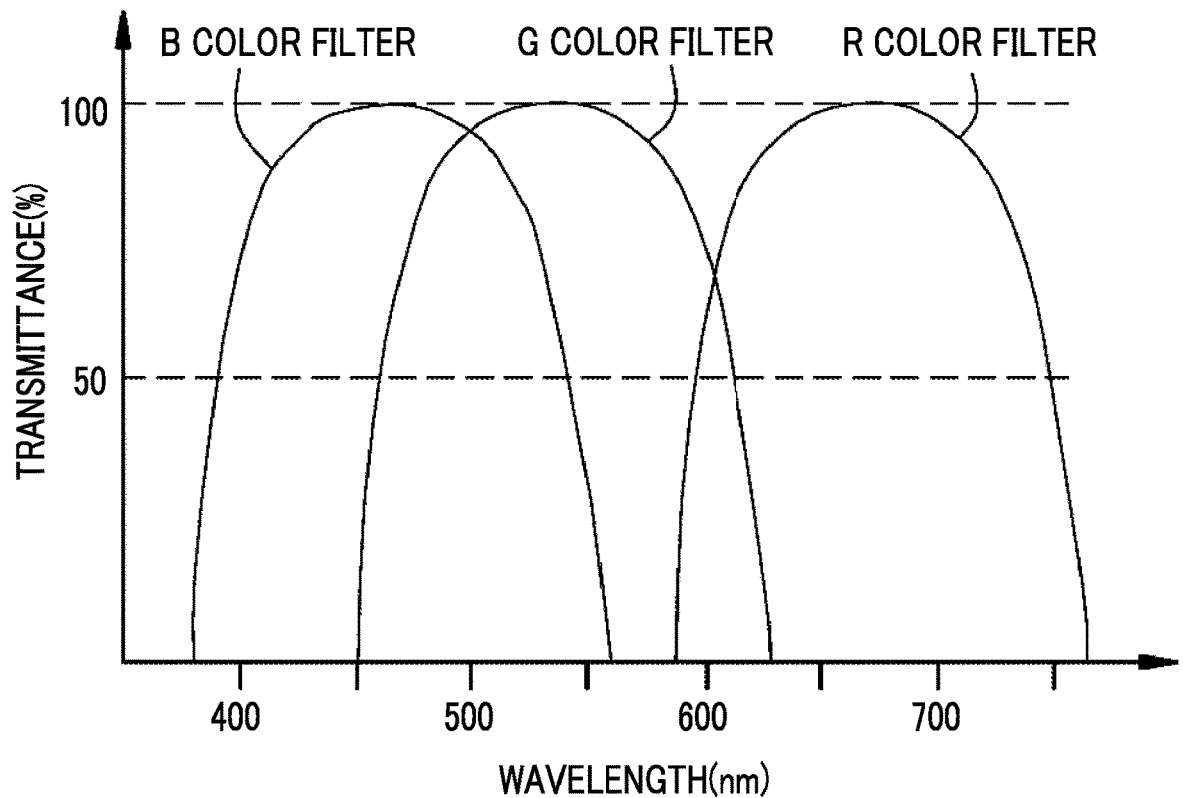
FIG. 5 is a graph illustrating the spectral transmittance of RGB color filters.

As illustrated in FIG. 5, the B color filter has a spectral transmittance of 380 to 560 nm, the G color filter has a spectral transmittance of 450 to 630 nm, and the R color filter has a spectral transmittance of 580 to 760 nm. Hence, in a case where the second white light is radiated to the observation target in the normal observation mode and the blood vessel thickness measurement mode, the second blue laser light and a portion of a green component of the second fluorescence enters the B pixel, a portion of a green component of the second fluorescence enters the G pixel, and a red component of the second fluorescence enters the R pixel.

Meanwhile, in a case where the first white light is radiated to the observation target in the oxygen saturation mode and the blood vessel depth measurement mode, the first blue laser light and a portion of a green component of the first fluorescence enters the B pixel, the portion of the green component of the first fluorescence and the first blue laser light attenuated by the G color filter enters the G pixel, and a red component of the first fluorescence enters the R pixel. Since the emission intensity of the first blue laser light is extremely larger than that of the first fluorescence, most of a B image signal output from the B pixel is occupied by a reflected light component of the first blue laser light. In the oxygen saturation mode and the blood vessel depth measurement mode, a light incidence component in each of RGB pixels in a case where the second white light is radiated to the observation target is the same as that in the normal observation mode.

As the sensor 48, a so-called complementary color image sensor including complementary color filters in cyan (C), magenta (M), yellow (Y), and green (G) on the imaging surface may be used. In a case where the complementary color image sensor is used as the sensor 48, a color converting unit for color-converting image signals in three colors of RGB from image signals in four colors of CMYG may be provided at the endoscope 12, the light source device 14, or the processor device 16. Even in a case where the complementary color image sensor is used in this way, image signals in three colors of RGB can be obtained by color conversion from the image signals in four colors of CMYG An imaging control unit 49 performs imaging control of the sensor 48. In the normal observation mode and the blood vessel thickness measurement mode, the observation target illuminated with the second white light is imaged by the sensor 48 in each one frame period (simply referred to as one frame). Accordingly, in each one frame, the sensor 48 outputs an Rc image signal from the R pixel, outputs a Gc image signal from the G pixel, and outputs a Bc image signal from the B pixel.

In the oxygen saturation mode and the blood vessel depth measurement mode, the imaging control unit 49 performs a control such that the sensor 48 performs imaging in synchronization with the light emission timings of the first white light and the second white light. Specifically, the sensor 48 reads signal charges obtained by imaging the observation target with the first white light, outputs an R1 image signal from the R pixel, outputs a G1 image signal from the G pixel, and outputs a B1 image signal from the B pixel. Also, the sensor 2 reads signal charges obtained by imaging the observation target with the second white light in a reading period of a second frame, outputs an R2 image signal from the R pixel, outputs a G2 image signal from the G pixel, and outputs a B2 image signal from the B pixel.

As illustrated in FIG. 2, image signals in respective colors output from the sensor 48 are transmitted to a correlated double sampling (CDS)/automatic gain control (AGC) circuit 50 (refer to FIG. 2). The CDS/AGC circuit 50 performs correlated double sampling (CDS) and automatic gain control (AGC) on the analog image signals output from the sensor 48. The image signals that have passed through the CDS/AGC circuit 50 are converted into digital image signals by an analog/digital (A/D) converter 52. The image signals digitized in this way are input to the processor device 16.

The processor device 16 includes an image signal acquisition unit 54 (corresponding to an "image acquisition unit" of the embodiment of the invention), a digital signal processor (DSP) 56, a noise reduction unit 58, a signal conversion unit 59, an image processing switching unit 60, a normal observation image processing unit 62, an oxygen saturation measurement unit 64 (corresponding to a "blood vessel index value variation factor measurement unit" of the embodiment of the invention), an oxygen saturation image generation unit 65, a blood vessel thickness measurement unit 66, a blood vessel thickness measurement image generation unit 67, a blood vessel depth measurement unit 68 (corresponding to a "blood vessel index value variation factor measurement unit" of the embodiment of the invention), a blood vessel depth measurement image generation unit 69, and a video signal generation unit 70.

The image signal acquisition unit 54 acquires the image signals output from the sensor 48 of the endoscope 12. The DSP 56 performs various kinds of signal processing, such as defect correction processing, offset processing, gain correction processing, linear matrix processing, gamma conversion processing, demosaicing processing, and YC conversion processing, on the acquired image signals. In the defect correction processing, signals of defective pixels of the sensor 48 are corrected. In the offset processing, dark current components are removed from the image signals subjected to the defect correction processing, and accurate zero levels are set. In the gain correction processing, the signal levels of the respective image signals are adjusted by multiplying the respective RGB image signals after the offset processing by a specific gain. The linear matrix processing for enhancing color reproducibility is performed on the respective color image signals after the gain correction processing.

Thereafter, the brightness and the saturation of the respective image signals are adjusted by the gamma conversion processing. The demosaicing processing (also referred to as equalization processing or synchronization processing) is performed on the image signals after the linear matrix processing, and signals of missing colors of the respective pixels are created by interpolation. By means of the demosaicing processing, all pixels have respective RGB color signals. The DSP 56 performs the YC conversion processing on the respective image signals after the demosaicing processing, and outputs a brightness signal Y and color difference signals Cb and Cr generated by the YC conversion processing to the noise reduction unit 58.

The noise reduction unit 58 performs noise reduction processing using, for example, a moving average method, a median filter method, or the like on the image signals subjected to the demosaicing processing or the like by the DSP 56. The image signals of which the noise has been reduced are input to the signal conversion unit 59, reconverted into RGB image signals, and then input to the image processing switching unit 60.

The image processing switching unit 60 inputs the image signals passed through the signal conversion unit 59 to the normal observation image processing unit 62 in a case where the normal observation mode is set. Additionally, in a case where the oxygen saturation mode is set, the image processing switching unit 60 inputs the image signals passed through the signal conversion unit 59 to the oxygen saturation measurement unit 64. Additionally, in a case where the blood vessel thickness measurement mode is set, the image processing switching unit 60 inputs the image signals passed through the signal conversion unit 59 to the blood vessel thickness measurement unit 66. Additionally, in a case where the blood vessel depth measurement mode is set, the image processing switching unit 60 inputs the image signals passed through the signal conversion unit 59 to the blood vessel depth measurement unit 68.

The normal observation image processing unit 62 generates RGB image data in which the input Rc image signal, Gc image signal, and Bc image signal equivalent to one frame are allotted to the R pixel, the G pixel, and the B pixel, respectively. Also, color conversion processing, such as 3×3 matrix processing, gradation transformation processing, and three-dimensional LUT processing, is performed on the RGB image data. Also, various kinds of color enhancement processing are performed on the RGB image data subjected to the color conversion processing. Structure enhancement processing, such as spatial frequency enhancement, is performed on the RGB image data subjected to the color enhancement processing. The RGB image data subjected to the structure enhancement processing is input to the video signal generation unit 70 as a normal observation image. In the video signal generation unit 70, the input normal observation image is converted into video signals (for example, the brightness signal Y and the color difference signals Cb and Cr), and the video signals after the conversion are output to the monitor 18. Accordingly, the normal observation image is displayed on the monitor 18.

The oxygen saturation measurement unit 64 measures the oxygen saturation of hemoglobin in blood on the basis of the input B1 image signal, G1 image signal, R1 image signal, B2 image signal, G2 image signal, and R2 image signal equivalent to two frames. The information on the measured oxygen saturation is sent to the oxygen saturation image generation unit 65. The oxygen saturation image generation unit 65 generates an oxygen saturation image colored in accordance with the oxygen saturation. The generated oxygen saturation image is input to the video signal generation unit 70. The video signal generation unit 70 converts the input oxygen saturation image into video signals and outputs the video signals after the conversion to the monitor 18. Accordingly, the oxygen saturation image is displayed on the monitor 18. In addition, the details of the oxygen saturation measurement unit 64 and the oxygen saturation image generation unit 65 will be described below.

The blood vessel thickness measurement unit 66 measures the blood vessel thickness of a blood vessel designated by a user on the basis of the input Bc image signal, Gc image signal, and Rc image signal equivalent to one frame. Here, the thickness (vessel diameter) of a blood vessel is a distance between a blood vessel and a boundary line of a mucous membrane, and is counted, for example, by counting the number of pixels in a lateral direction of the blood vessel through the blood vessel from an edge of the blood vessel. Hence, the thickness of a blood vessel is the number of pixels. However, in a case where an imaging distance, a zoom magnification factor, and the like in a case where an image is captured are known, the thickness can be converted in the unit of length, such as "µm" in a case where necessary.

The information on the blood vessel thickness measured by the blood vessel thickness measurement unit 66 and the Bc image signal, the Gc image signal, and the Rc image signal equivalent to one frame are sent to the blood vessel thickness measurement image generation unit 67. The blood vessel thickness measurement image generation unit 67 generates a blood vessel thickness measurement image in which the information on the blood vessel thickness is overlappingly displayed on the image of the observation target. The generated blood vessel thickness measurement image is input to the video signal generation unit 70. The video signal generation unit 70 converts the input blood vessel thickness measurement image into video signals and outputs the video signals after the conversion to the monitor 18. Accordingly, the blood vessel thickness measurement image is displayed on the monitor 18. In addition, the details of the blood vessel thickness measurement unit 66 and the blood vessel thickness measurement image generation unit 67 will be described below.

The blood vessel depth measurement unit 68 measures the blood vessel depth of the blood vessel designated by the user on the basis of the input B1 image signal, G1 image signal, R1 image signal, B2 image signal, G2 image signal, and R2 image signal equivalent to two frames. The information on the measured blood vessel depth, the B2 image signal, the G2 image signal, and the R2 image signal are sent to the blood vessel depth measurement image generation unit 69. The blood vessel depth measurement image generation unit 69 generates a blood vessel depth measurement image in which the information on the blood vessel depth is overlappingly displayed on the image of the observation target. The generated blood vessel depth measurement image is input to the video signal generation unit 70. The video signal generation unit 70 converts the input blood vessel depth measurement image into video signals and outputs the video signals after the conversion to the monitor 18. Accordingly, the blood vessel depth measurement image is displayed on the monitor 18. In addition, the details of the blood vessel depth measurement unit 68 and the blood vessel depth measurement image generation unit 69 will be described below.

Figure 6:
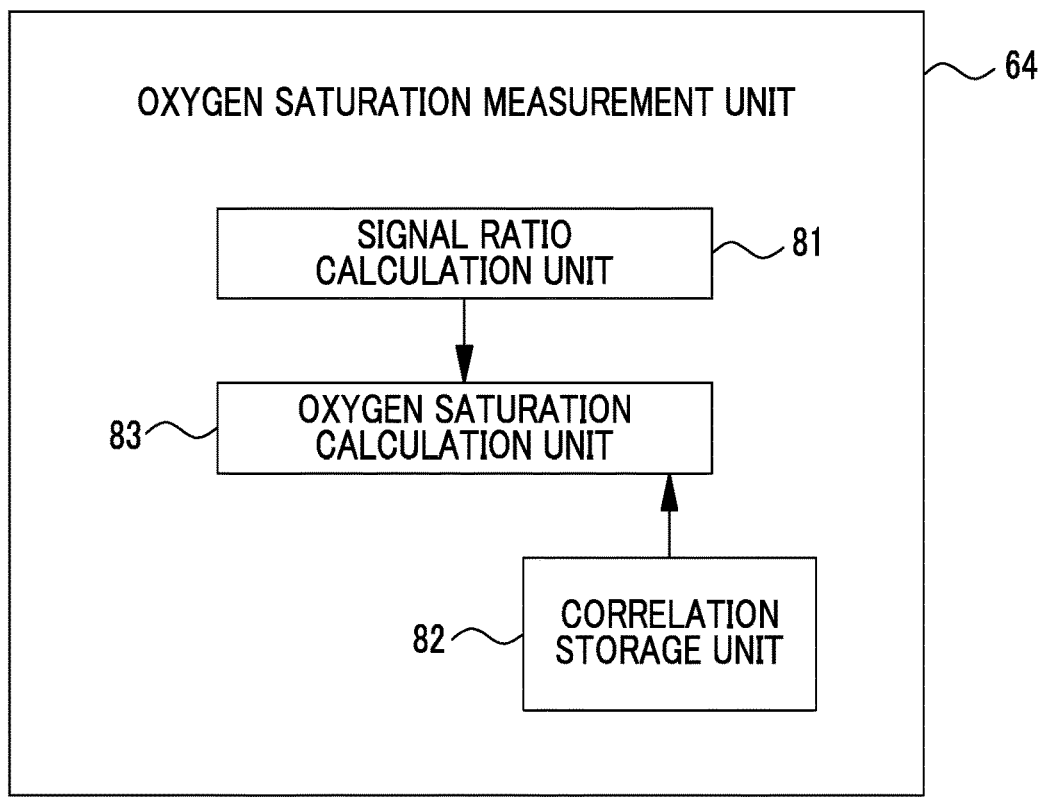
FIG. 6 is a block diagram illustrating the functions of an oxygen saturation measurement unit.

As illustrated in FIG. 6, the oxygen saturation measurement unit 64 has a signal ratio calculation unit 81, a correlation storage unit 82, and an oxygen saturation calculation unit 83. The signal ratio calculation unit 81 calculates a signal ratio B1/G2 of the B1 image signal and the G2 image signal for each pixel and calculates a signal ratio R2/G2 of an R2 image signal and the G2 image signal for each pixel. In addition, in a case where the signal ratio B1/G2 is calculated, it is preferable that the signal ratio calculation unit 81 performs the correction processing of removing a signal value resulting from the first fluorescence from the B1 image signal to enhance color separability, through an inter-pixel calculation using the B1 image signal, the G1 image signal, and the R1 image signal, and uses the B1 image signal obtained by correcting a signal value resulting from substantially the first blue laser light only.

Figure 7:
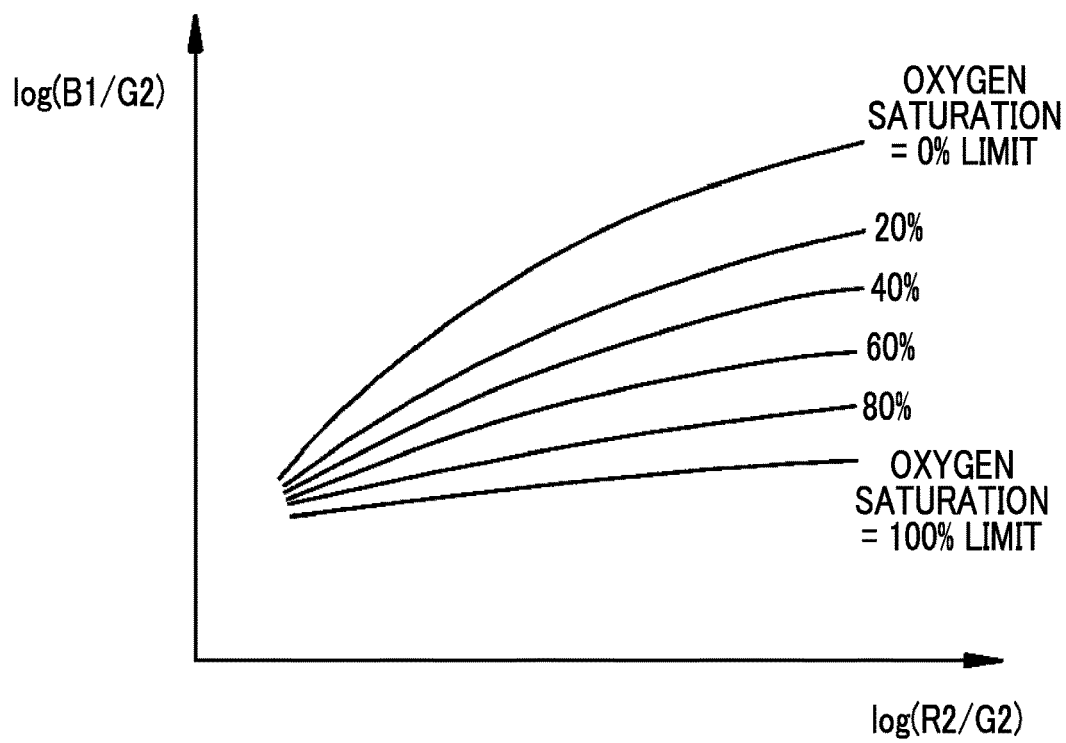
FIG. 7 is a graph illustrating a correlation between a signal ratio and an oxygen saturation.

The correlation storage unit 82 stores a correlation between the signal ratios calculated by the signal ratio calculation unit 81, and the oxygen saturation. This correlation is stored in a two-dimensional table in which isolines of the oxygen saturation are defined on a two-dimensional space illustrated in FIG. 7. In addition, the positions and the shapes of the isolines with respect to the signal ratios are obtained in advance by physical simulation of light scattering, and the intervals of the respective isolines vary in accordance with the amount of blood (lateral axis of FIG. 7). The correlation between the signal ratios and the oxygen saturation is stored on log scales.

Figure 8:
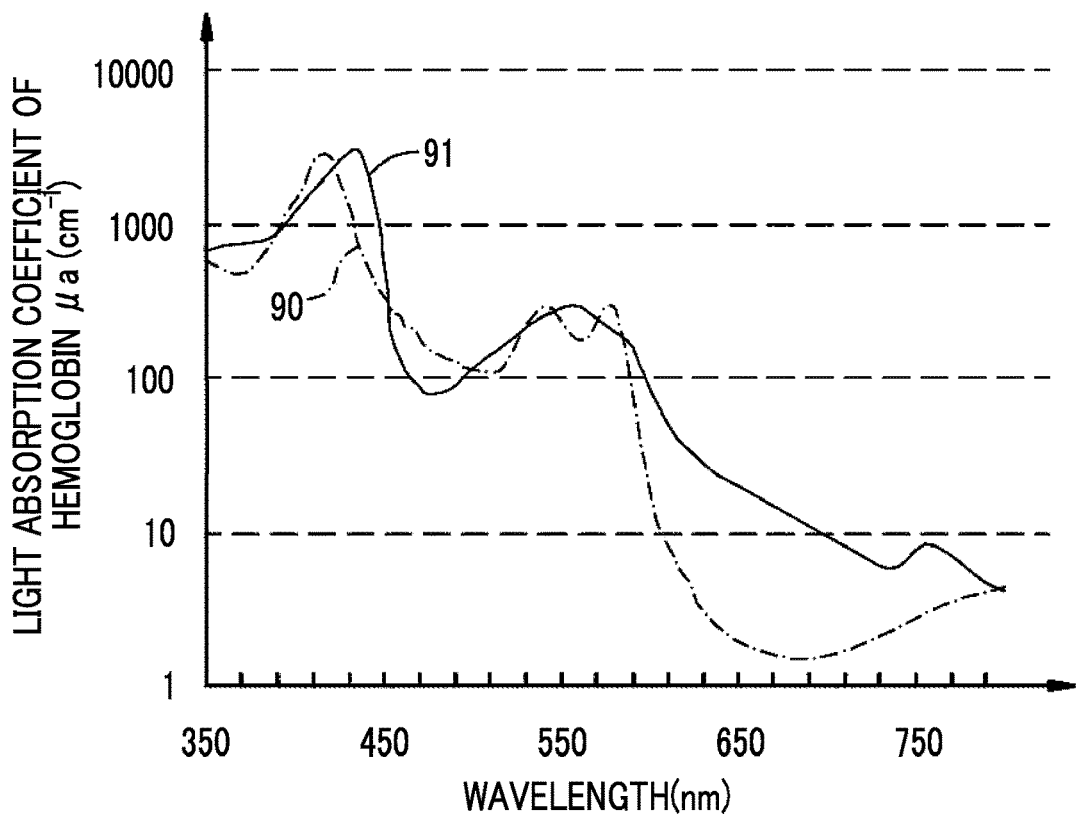
FIG. 8 is a graph illustrating light absorption coefficients of oxygenated hemoglobin and reduced hemoglobin.

As illustrated in FIG. 8, the above correlation is closely correlated with light-absorption characteristics and light-scattering characteristics of oxygenated hemoglobin (graph 90) and reduced hemoglobin (graph 91). For example, in a wavelength range with a large difference between the light absorption coefficients of the oxygenated hemoglobin and the reduced hemoglobin, that is, a wavelength range in which the light absorption coefficients vary in accordance with the oxygen saturation of hemoglobin in blood like a wavelength range in the vicinity of the central wavelength 473 nm of the first blue laser light, it is easy to handle information on the oxygen saturation. However, the B1 image signal including a signal corresponding to 473 nm light has a high dependence not only on the oxygen saturation but the amount of blood. Thus, in addition to the B1 image signal, by using the signal ratio R2/G2 obtained from the G2 image signal corresponding to the light varying mainly depending on the amount of blood and the R2 image signal used as a reference signal of the B1 image signal and the G2 image signal, the oxygen saturation can be accurately obtained without being dependent on the amount of blood.

Figure 9:
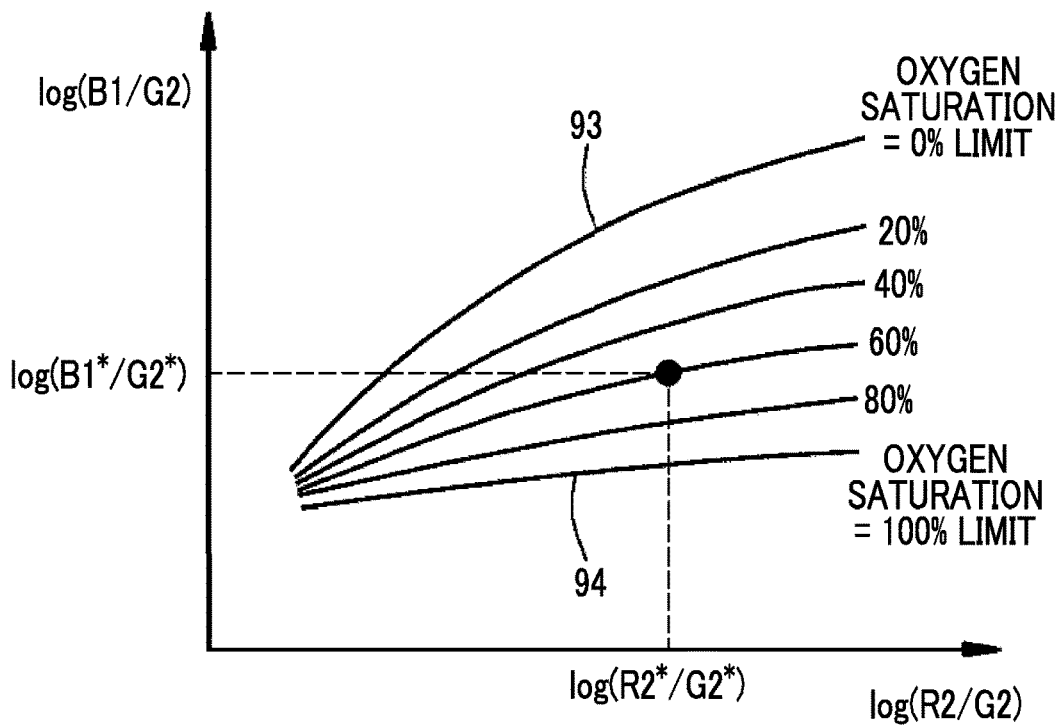
FIG. 9 is an illustrative view illustrating a method of calculating the oxygen saturation.

The oxygen saturation calculation unit 83 calculates the oxygen saturation on the basis of the image signals by using the signal ratios calculated in the signal ratio calculation unit 81. More specifically, the oxygen saturation calculation unit 83 refers the correlation stored in the correlation storage unit 82, and calculates the oxygen saturation corresponding to the signal ratios calculated by the signal ratio calculation unit 81 for each pixel. For example, in a case where a correlation is referred to as illustrated in FIG. 9 in a case where the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%". Hence, the oxygen saturation calculation unit 83 calculates the oxygen saturation of this specific pixel as "60%".

In addition, the signal ratio B1/G2 and the signal ratio R2/G2 hardly become extremely large or extremely small. That is, the values of the signal ratio B1/G2 and the signal ratio R2/G2 hardly exceed a lower limit line 93 of an oxygen saturation of 0% or on the contrary fall below an upper limit line 94 of an oxygen saturation of 100%. However, the oxygen saturation calculation unit 83 sets the oxygen saturation to 0% in a case where the oxygen saturation to be calculated falls below than the lower limit line 93 and sets the oxygen saturation to 100% in a case where the oxygen saturation exceeds the upper limit line 94. Additionally, in a case where points corresponding to the signal ratio B1/G2 and the signal ratio R2/G2 deviate from between the lower limit line 93 and the upper limit line 94, a display may be performed such that it can be seen that the reliability of the oxygen saturation in the pixel is low, and the oxygen saturation may not be calculated.

The oxygen saturation image generation unit 65 generates the oxygen saturation image obtained by coloring the oxygen saturation, using the oxygen saturation calculated in the oxygen saturation calculation unit 83. Specifically, first, the oxygen saturation image generation unit 65 generates a base image by the same generation method as that for the normal observation image, on the basis of the R2 image signal, the G2 image signal, and the B2 image signal. Then, the coloring processing of changing the colors of the base image in accordance with the oxygen saturation is performed on the base image. Accordingly, the oxygen saturation image is obtained. In addition, in the coloring processing, for example, it is preferable not to change the colors of the base image regarding a pixel region where the oxygen saturation exceeds a specific threshold value (for example, 70%) and to change the colors of the base image in accordance with the oxygen saturation regarding a pixel region where the oxygen saturation falls below the specific threshold value.

Additionally, the oxygen saturation image may be generated using a method separate from the above. For example, in a case where the oxygen saturation image is generated using the brightness signal Y and the color difference signals Cr and Cb, it is preferable to change a signal level in accordance with the G2 image signal regarding the brightness signal Y and to change signal levels in accordance with the oxygen saturation regarding the color difference signals Cr and Cb. For example, it is preferable to set the signal level of Cr to "positive" and set the signal level of Cb to "negative" in a case where the oxygen saturation is high, while it is preferable to set the signal level of Cr to "negative" and set the signal level of Cb to "positive" in a case where the oxygen saturation is low. In this case, in the oxygen saturation image, a high oxygen region is displayed in red, while a low oxygen region is displayed in blue.

Figure 10:
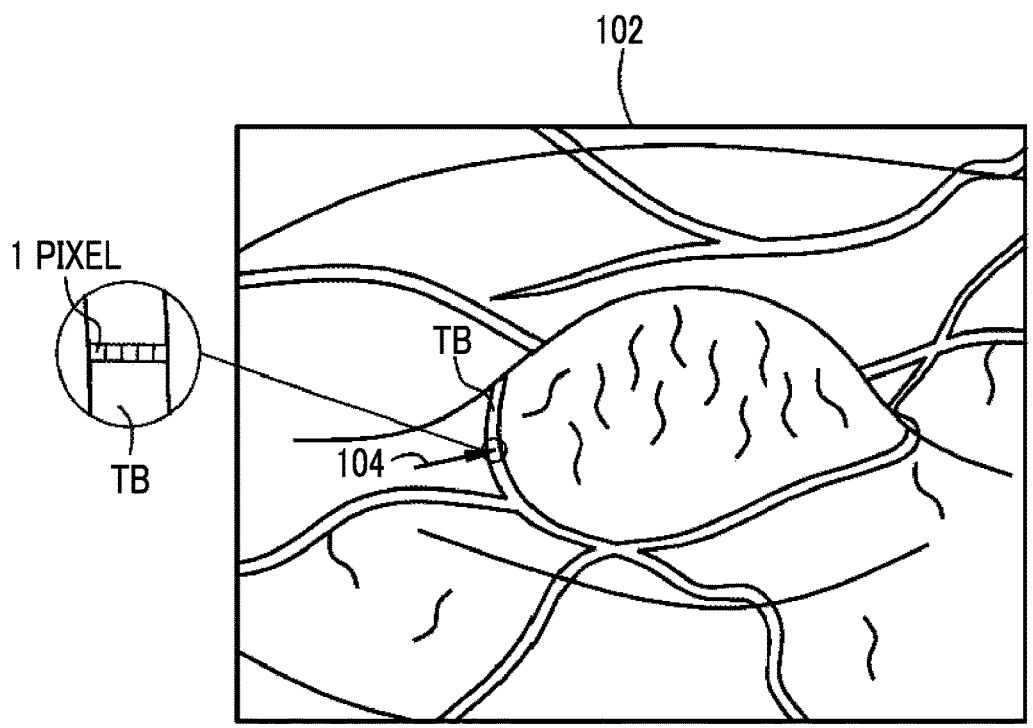
FIG. 10 is an image view illustrating a blood vessel selection image.

The blood vessel thickness measurement unit 66 measures the blood vessel thickness of a specific blood vessel on the basis of the Rc image signal, the Gc image signal, and the Bc image signal. The blood vessel thickness measurement unit 66 transmits the Rc image signal, the Gc image signal, and the Bc image signal to a measurement target blood vessel designation unit 100 in order to designate a measurement target blood vessel to be a measurement target for the blood vessel thickness (refer to FIG. 2). As illustrated in FIG. 10, the measurement target blood vessel designation unit 100 generates a blood vessel selection image 102 for selecting the measurement target blood vessel, on the basis of the Rc image signal, the Gc image signal, and the Bc image signal, to display the generated blood vessel selection image on the monitor 18. It is preferable that the blood vessel selection image 102 is an image obtained by extracting a blood vessel by the binarization processing which distinguishes the blood vessel and the other portions. The user operates a selection pointer 104 on the blood vessel selection image 102 by an operating member, such as the console 20, and designates a measurement target blood vessel TB with the selection pointer 104. The blood vessel thickness measurement unit 66 transmits the information on the measurement target blood vessel TB designated by the operating member, such as the console 20, to the measurement target blood vessel designation unit 100.

The blood vessel thickness measurement unit 66 specifies pixels of a portion in which the measurement target blood vessel is present among the Rc image signal, the Gc image signal, and the Bc image signal in a case where the measurement target blood vessel is designated. The blood vessel thickness of the measurement target blood vessel is calculated from the specified pixels. Specifically, by multiplying the number of the specified pixels (for example, the pixel number is "5 pixels" in the case of FIG. 10) by the average size of one pixel, the blood vessel thickness of the measurement target blood vessel is calculated. In addition, since the blood vessel thickness is influenced by an observation distance between the observation target and the distal end part 24 of the endoscope, it is preferable that the size of one pixel is determined in accordance with the observation distance.

Figure 11:
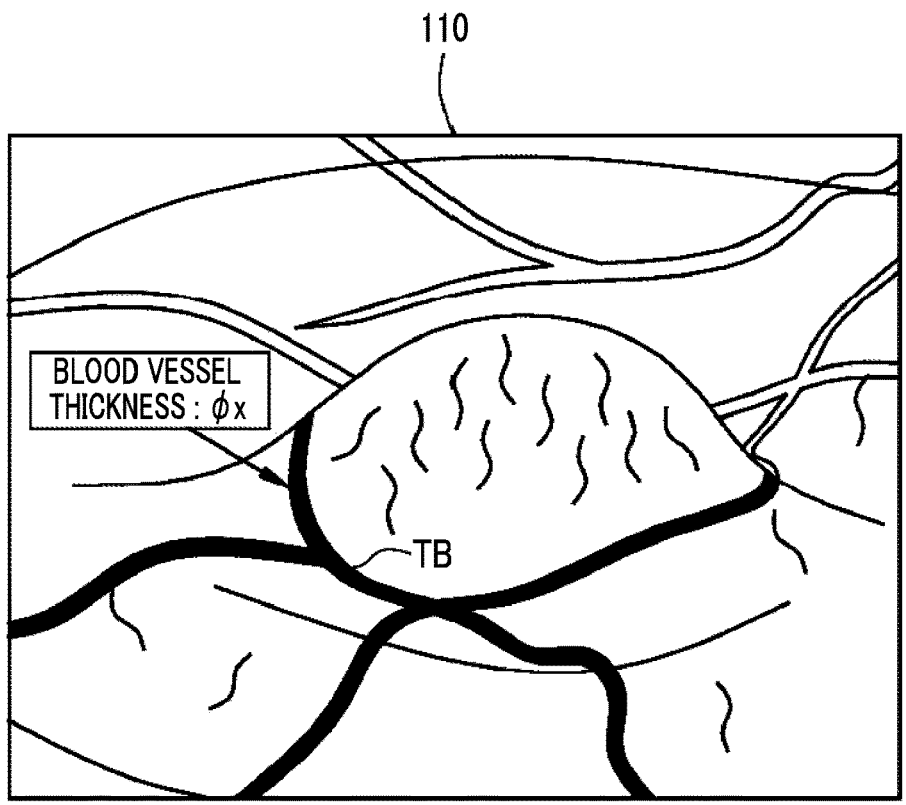
FIG. 11 is an image view illustrating a blood vessel thickness measurement image.

The blood vessel thickness measurement image generation unit 67 generates the base image through the same generation method as that for the normal observation image, on the basis of the Rc image signal, the Gc image signal, and the Bc image signal. Also, the blood vessel thickness measurement image generation unit 67 performs the processing of displaying the measurement target blood vessel in an enhanced manner and overlappingly displaying the blood vessel thickness of the measurement target blood vessel, on the base image. Accordingly, as illustrated in FIG. 11, a blood vessel thickness measurement image 110 in which the measurement target blood vessel TB displayed in an enhanced manner and a blood vessel thickness $\phi x$ of the measurement target blood vessel TB is displayed is obtained.

Figure 12:
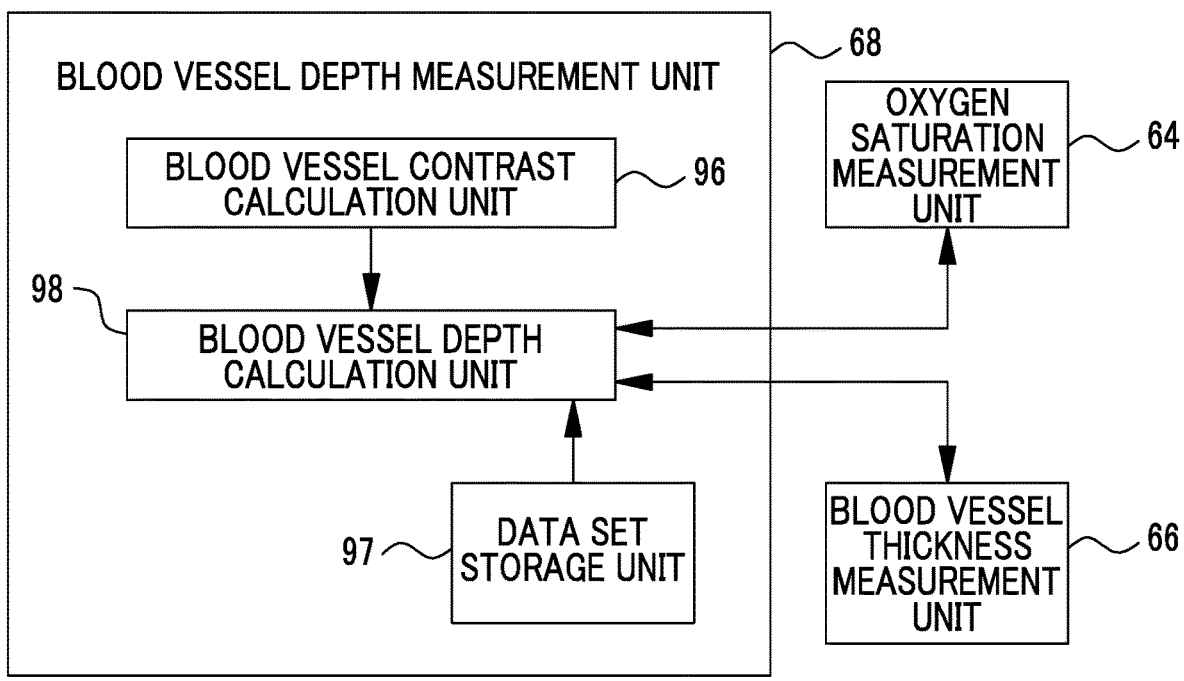
FIG. 12 is a block diagram illustrating functions of a blood vessel depth measurement unit.

As illustrated in FIG. 12, the blood vessel depth measurement unit 68 includes a blood vessel contrast calculation unit 96 (corresponding to a "blood vessel index value calculation unit" of the embodiment of the invention), a data set storage unit 97, and a blood vessel depth calculation unit 98. The blood vessel depth calculation unit 98 also designates a measurement target blood vessel to be a measurement target for the blood vessel depth, similarly to the blood vessel thickness measurement unit 66. The designation of the measurement target blood vessel is performed by the measurement target blood vessel designation unit 100, similarly to the above. In addition, it is preferable that the measurement target blood vessel designation unit 100 generates a blood vessel selection image on the basis of the B2 image signal, the G2 image signal, and the R2 image signal.

The blood vessel contrast calculation unit 96 calculates a pixel value Ib of a blood vessel, and a pixel value Im of a portion other than the blood vessel, such as the mucous membrane, (for example, an average value of pixel values of the mucous membrane), on the basis of a blood vessel contrast image signal (corresponding to a blood vessel index value i mage" of the embodiment of the invention) among the input image signals. The blood vessel contrast calculation unit 96 uses the blood vessel contrast image signal including multiple-wavelength image signals (corresponding to "multiple-wavelength images" of the embodiment of the invention). The multiple-wavelength image signals are constituted of multiple image signals having wavelength components that are different from each other, and correspond to the R2 image signal, the G2 image signal, and the B2 image signal in the present embodiment. Also, the blood vessel contrast calculation unit 96 calculates the blood vessel contrast Ct according to the following Equation.

$$Ct=-\text{Log}(Ib/Im) \quad \text{Equation)}$$

In addition, in the following, the blood vessel contrast Ct of the measurement target blood vessel is defined as "Ct*".

As illustrated in FIG. 13, the data set storage unit 97 stores a data set 120 constituted measurement data in which the blood vessel contrast Ct, and the oxygen saturation, the blood vessel thickness and the blood vessel depth in a case where the blood vessel contrast Ct is obtained are associated with each other. In the case of FIG. 13, the measurement data is stored for each level of the oxygen saturation. Specifically, regarding the measurement data in a case where the oxygen saturation is 100%, measurement data in which a minimum blood vessel thickness $\phi 1$ within a blood vessel thickness measurable range, a shallowest blood vessel depth d1 within a blood vessel depth measurable range, and a blood vessel contrast Ct (100, $\phi 1$, d1) obtained in the case of the blood vessel thickness $\phi 1$ and the blood vessel depth d1 are associated with each other is stored.

Similarly, measurement data in which all combinations of blood vessel depths P2 to Pn with respect to the minimum blood vessel thickness $\phi 1$ and blood vessel contrasts Ct (100, $\phi 1$, d2) to Ct (100, $\phi 1$, dn) obtained in a case where these are combined are associated with each other is also stored. Additionally, measurement data in which the same association as above is also performed on the blood vessel thicknesses $\phi 2$ to $\phi m$ in the case where the oxygen saturation is 100% is stored. Moreover, measurement data in which the same association as above is also performed in cases where the oxygen saturation is 0% to 99% is stored.

Figure 14:
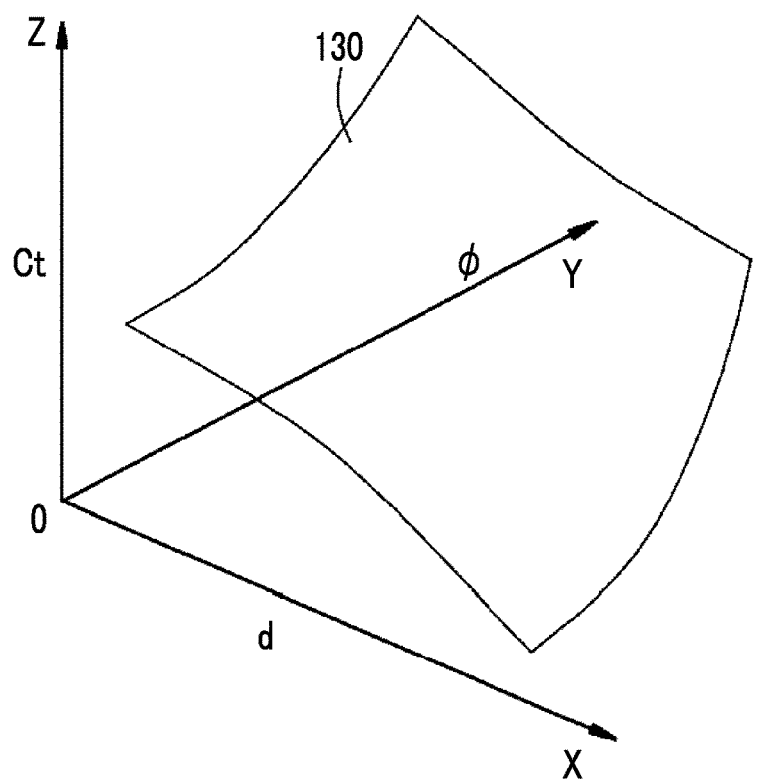
FIG. 14 is a graph illustrating a plane on a three-dimensional space showing a relationship among blood vessel thickness $\phi$, blood vessel depth d, and blood vessel contrast Ct in a case where the oxygen saturation has a specific value $s^*$.

In addition, a relationship between the blood vessel contrast Ct, and an oxygen saturation s, the blood vessel thickness $\phi$, and the blood vessel depth d can be expressed by a function Ct=f (s, $\phi$, d). This function Ct=f (s, $\phi$, d) is expressed by a plane 130 as illustrated in FIG. 14 on a three-dimensional space where the blood vessel depth d is defined an X axis, the blood vessel thickness $\phi$ is defined as a Y axis, and the blood vessel contrast Ct is defined as a Z axis in a case where the oxygen saturation s is fixed to a specific value. In FIG. 14, it can be seen that, as the blood vessel depth is deeper and the blood vessel thickness is thinner, the blood vessel contrast is lower. On the other hand, it can be seen that, as the blood vessel depth is shallower and the blood vessel thickness is thicker, the blood vessel contrast is higher.

The blood vessel contrast calculation unit 96 calculates the blood vessel depth of the specific blood vessel by using the blood vessel contrast Ct* calculated by the blood vessel depth calculation unit 98 and the B1 image signal, the B2 image signal, the G2 image signal, and the R2 image signal equivalent to two frames and referring to the data set stored in the data set storage unit 97.

The blood vessel depth calculation unit 98 sends the B1 image signal, the G2 image signal, and the R2 image signal to the oxygen saturation measurement unit 64, and an oxygen saturation s* of the measurement target blood vessel is measured in the oxygen saturation measurement unit 64. The information on the measured oxygen saturation s* of the measurement target blood vessel is returned to the blood vessel depth calculation unit 98. Additionally, the blood vessel depth calculation unit 98 sends the B2 image signal, the G2 image signal, and the R2 image signal to the blood vessel thickness measurement unit 66, and a blood vessel thickness $\phi$* of the measurement target blood vessel is measured in the blood vessel thickness measurement unit 66.

In a case where the oxygen saturation s and the blood vessel thickness $\phi$* of the measurement target blood vessel are obtained, the blood vessel depth calculation unit 98 narrows the measurement data corresponding to the oxygen saturation s* and the blood vessel thickness $\phi$* of the measurement target blood vessel as a first sub-data set, from the data set stored in the data set storage unit 97. For example, in a case where the oxygen saturation s* of the measurement target blood vessel is 100% and the blood vessel thickness $\phi$* is $\phi 1$, measurement data of a portion corresponding to the oxygen saturation 100% and the blood vessel thickness $\phi 1$ is selected as the first sub-data set from the data set (refer to FIG. 13).

In a case where the first sub-data set is narrowed, the blood vessel depth calculation unit 98 calculates a blood vessel depth corresponding to the blood vessel contrast Ct* calculated by the blood vessel contrast calculation unit 96 with reference to the first sub-data set. This calculated blood vessel depth becomes the blood vessel depth of the measurement target blood vessel. For example, in a case where the calculated blood vessel depth is narrowed to the first sub-data set illustrated in FIG. 13, in the first sub-data set, the blood vessel depth corresponding to the blood vessel contrast Ct* becomes "d*". As described above, since the blood vessel depth of the measurement target blood vessel is calculated using not only the blood vessel contrast but also the oxygen saturation measured in the oxygen saturation measurement unit 64, the blood vessel thickness measured in the blood vessel thickness measurement unit 66, and the measurement data in which the blood vessel contrast, the oxygen saturation, the blood vessel thickness, and the blood vessel depth are associated with each other, the calculation accuracy of the calculated blood vessel depth is high compared to a case where calculation is performed only with the blood vessel contrast.

In addition, a method of calculating the blood vessel depth in a case where the relationship between the blood vessel contrast Ct, and the oxygen saturation s, the blood vessel thickness $\phi$, and the blood vessel depth d is expressed by the above-described three-variable function Ct=f (s, $\phi$, d) is as follows. First, in a case where the oxygen saturation s* of the measurement target blood vessel is fixed, the functions Ct=f (s*, $\phi$, d) becomes a two-variable function regarding the blood vessel thickness $\phi$ and the blood vessel depth d. In a case where this two-variable function is expressed by the above three-dimensional space, the two-variable function is expressed by the plane 130 illustrated in FIG. 14. Moreover, in a case where the blood vessel thickness $\phi$* is fixed, the blood vessel thickness $\phi$* becomes a one-variable function Ct=f (s*, $\phi$*, d) regarding the blood vessel depth d.

Figure 15:
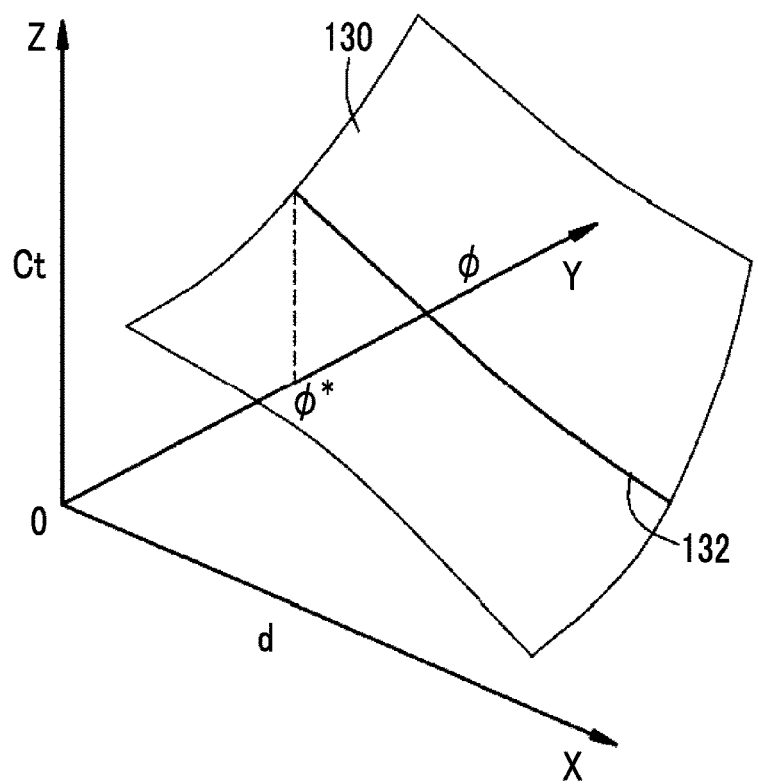
FIG. 15 is a graph illustrating the plane on the three-dimensional space showing the relationship among the blood vessel thickness ϕ, the blood vessel depth d, and the blood vessel contrast Ct in a case where the oxygen saturation has the specific value s*, and is a graph showing a cross-section illustrating a portion that is the blood vessel thickness ϕ* in the plane.
Figure 16:
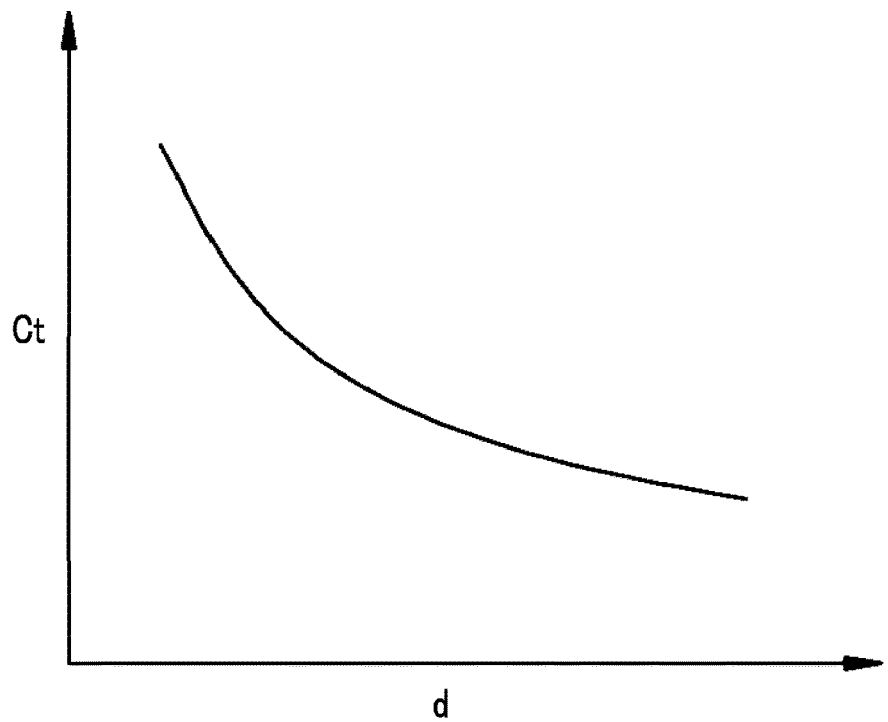
FIG. 16 is a graph illustrating a relation line on a two-dimensional space showing a relationship among the blood vessel depth d, the blood vessel contrast Ct in a case where the oxygen saturation has the specific value s and the blood vessel thickness has a specific value ϕ*.

As illustrated in FIG. 15, this one-variable function becomes equal to a cross-section 132 in a case where the plane 130 showing the above two-variable function is cut in an X-axis direction in the portion of the blood vessel thickness cr. Additionally, in a case where the above one-variable function Ct=f (s*, $\phi$*, d) is expressed by a two-dimensional plane in which the blood vessel depth d is defined as the X axis and the blood vessel contrast Ct is defined as the Y axis, as illustrated in FIG. 16, the one-variable function is expressed by a function in which the blood vessel contrast Ct decreases as the blood vessel depth d is deeper. As described above, it is possible to calculate the blood vessel depth d* from the blood vessel contrast Ct* by being dropped into the one-variable function Ct=f (s*, ϕ*, d).

Figure 17:
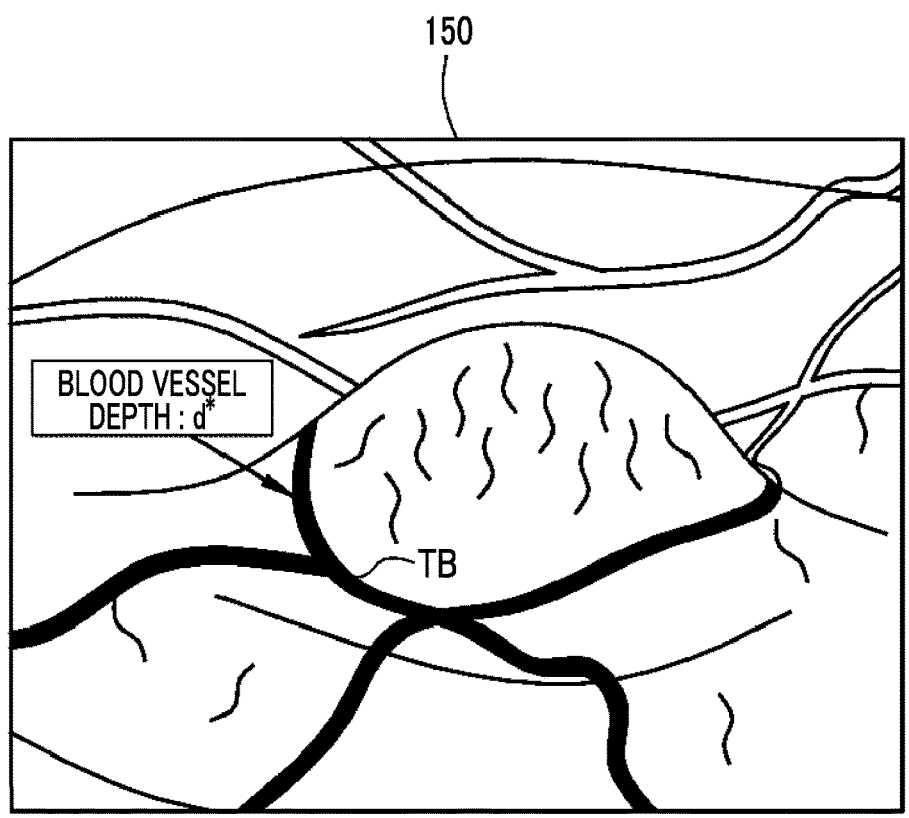
FIG. 17 is an image view illustrating a blood vessel depth measurement image.

The blood vessel depth measurement image generation unit 69 generates the base image by the same generation method as that for the normal observation image, on the basis of the R2 image signal, the G2 image signal, and the B2 image signal. Also, the blood vessel depth measurement image generation unit 69 performs the processing of displaying the measurement target blood vessel in an enhanced manner and overlappingly displaying the blood vessel depth of the measurement target blood vessel, on the base image. Accordingly, as illustrated in FIG. 17, a blood vessel depth measurement image 150 in which the measurement target blood vessel TB displayed in an enhanced manner and a blood vessel depth d* of the measurement target blood vessel TB is displayed is obtained.

Figure 18:
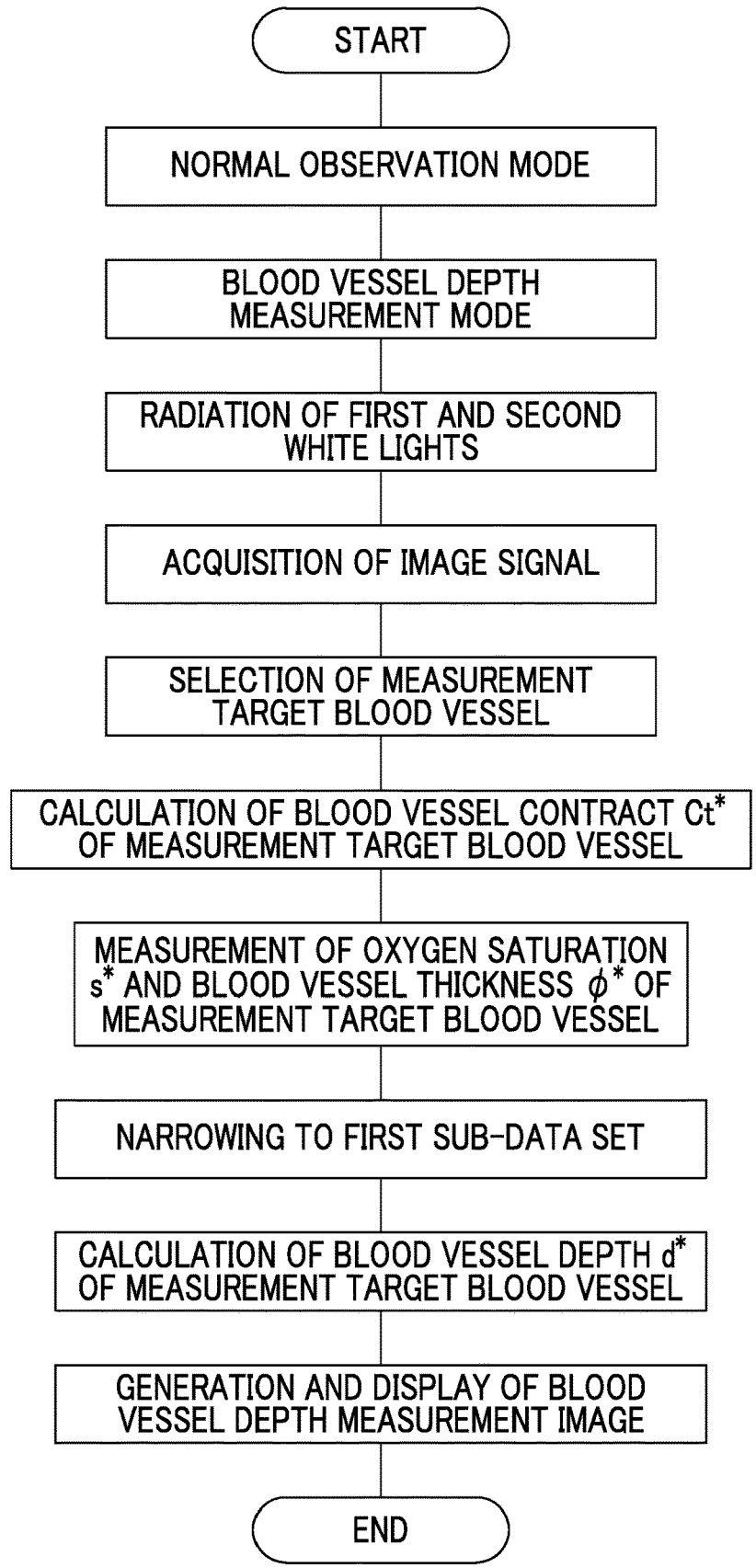
FIG. 18 is a flowchart illustrating the operation of the endoscopic system.

Next, a flow of observation by the endoscopic system 10 of the present embodiment will be described along with a flowchart of FIG. 18. First, in the normal observation mode, the user observes the observation target and detects a region with the possibility of a lesioned part. Then, in a case where the region with the possibility of the lesioned part is discovered, the mode changeover SW 22b is operated to switch to the blood vessel depth measurement mode in order to measure a blood vessel depth regarding a blood vessel in the region.

In a case where the switching to the blood vessel depth measurement mode is performed, the first and second white lights are alternately radiated to the observation target in synchronization with the imaging frame of the sensor 48. The sensor 48 outputs the R1 image signal, the G1 image signal, and B1 image signal in a first frame and outputs the R2 image signal, the G2 image signal, and the B2 image signal in the second frame. These image signals are acquired by the image signal acquisition unit 54 of the processor device 16 and are subjected to various kinds of signal processing.

Then, the blood vessel selection image 102 is generated on the basis of the R2 image signal, the G2 image signal, and the B2 image signal and is displayed on the monitor 18. The user selects the blood vessel of the portion with the possibility of the lesioned part in the blood vessel selection image 102 as the measurement target blood vessel. In a case where the measurement target blood vessel is selected, the blood vessel contrast calculation unit 96 calculates the blood vessel contrast Ct* of the measurement target blood vessel. Additionally, the B1 image signal, the G2 image signal, and the R2 image signal are sent to the oxygen saturation measurement unit 64, and the oxygen saturation s* of the measurement target blood vessel is measured by the oxygen saturation measurement unit 64. Additionally, the R2 image signal, the G2 image signal, and the B2 image signal are sent to the blood vessel thickness measurement unit 66, and the blood vessel thickness ϕ* of the measurement target blood vessel is measured by the blood vessel thickness measurement unit 66.

After the oxygen saturation s* and the blood vessel thickness ϕ* of the measurement target blood vessel are measured, the blood vessel depth calculation unit 98 narrows the measurement data corresponding to the oxygen saturation s* and the blood vessel thickness ϕ* of the measurement target blood vessel as the first sub-data set, from the data set stored in the data set storage unit 97. In a case where the first sub-data set is narrowed, the blood vessel depth calculation unit 98 calculates the blood vessel depth corresponding to the blood vessel contrast Ct* of the measurement target blood vessel as the blood vessel depth d* of the measurement target blood vessel with reference to the first sub-data set. In a case where the blood vessel depth d* of the measurement target blood vessel is calculated, the blood vessel depth measurement image is generated on the basis of the information on the blood vessel depth d* of a measurement target blood vessel, and the R2 image signal, the G2 image signal, and the B2 image signal and is displayed on the monitor 18.

In addition, in the above embodiment, weighting may be performed on the R2 image signal, the G2 image signal, and the B2 image signal in the blood vessel contrast calculation unit 96, and the blood vessel contrast of the measurement target blood vessel may be calculated on the basis of the weighted R2 image signal, G2 image signal, and B2 image signal. For example, in the blood vessel selection image 102, an approximate blood vessel depth (a visually measured blood vessel depth) of the measurement target blood vessel is measured by the user's viewing, and weighting according to the visually measured blood vessel depth) is performed. In addition, setting of the weighting is performed by the operating member, such as the console 20.

Here, in a case where the visually measured blood vessel depth is shallow, a blood vessel located in a shallow portion, such as a surface layer blood vessel, is often included in short-wavelength image signals. Therefore, the weighting of the B2 image signal included in the short-wavelength image signals is made larger than the weighting of the other G2 image signal and R2 image signal. On the other hand, in a case where the visually measured blood vessel depth is deep, a blood vessel located in a deep portion, such as a middle-depth layer blood vessel, is often included in long-wavelength image signals. Therefore, the weighting of the G2 image signal included in the long-wavelength image signals is made larger than the weighting of the other B2 image signal and R2 image signal. As described above, the calculation accuracy of the blood vessel contrast of the measurement target blood vessel can be improved by increasing the weighting of image signals within a wavelength range where the measurement target blood vessel is included. The improvement in the calculation accuracy of the blood vessel contrast also leads to an improvement in the calculation accuracy of the blood vessel depth.

Additionally, the blood vessel contrast calculation unit 96 may calculate the blood vessel contrast of the measurement target blood vessel by calculating the blood vessel contrast for each of the R2 image signal, G2 image signal, and B2 image signal and calculating the calculated blood vessel contrasts in combination. As a method of calculating the blood vessel contrasts in combination, for example, the weighting average processing of weighting the blood vessel contrasts and adding the blood vessel contrasts to each other can be considered. In a case where this weighting average processing is performed, it is preferable that weighting coefficients of the respective blood vessel contrasts are set on the basis of wavelength components of the image signals used for calculating the blood vessel contrasts.

For example, in a case where the weighting coefficient of a blood vessel contrast Ctr obtained from the R2 image signal is defined as a, the weighting coefficient of a blood vessel contrast Ctg obtained from the G2 image signal is defined as β, and the weighting coefficient of a blood vessel contrast Ctb obtained from the B2 image signal is defined as χ, the blood vessel contrast of the measurement target blood vessel is "α×Ctr+β×Ctg+χ×Ctb". In a case where the measurement target blood vessel is a surface layer blood vessel, it is preferable to make the weighting coefficient χ larger than the other weighting coefficients α and β. In addition, the respective blood vessel contrasts Ctr, Ctg, and Ctb represent the blood vessel contrasts of the same blood vessel of interest, respectively.

Figure 19:
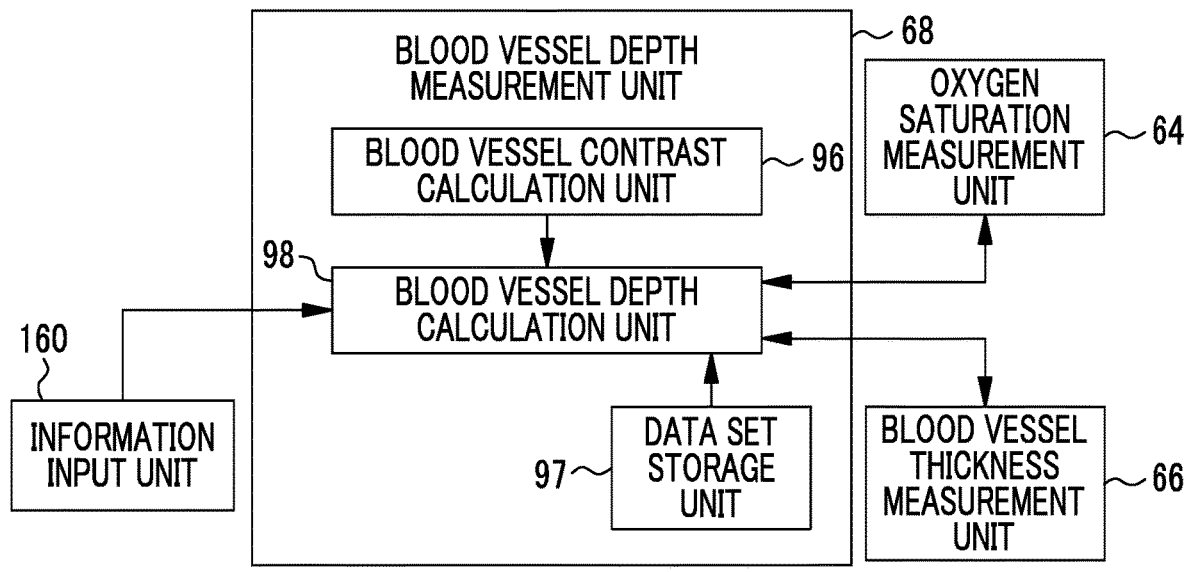
FIG. 19 is a block diagram illustrating the functions of a blood vessel depth measurement unit to which an information input unit is connected.

In addition, in the above embodiment, the first sub-data set having the oxygen saturation s* and the blood vessel thickness φ* of the measurement target blood vessel is narrowed using the oxygen saturation s* of the measurement target blood vessel measured in the oxygen saturation measurement unit 64 and the blood vessel thickness φ* of the measurement target blood vessel measured in the blood vessel thickness measurement unit 66. However, the sub-data set may be narrowed by the other methods. For example, as illustrated in FIG. 19, after an oxygen saturation s and a blood vessel thickness φ of the measurement target blood vessel are manually input by an information input unit 160 connected to the blood vessel depth calculation unit 98, the blood vessel depth calculation unit 98 narrows the measurement data having the input oxygen saturation s and blood vessel thickness φ of the measurement target blood vessel as a second sub-data set. Even in the case of this second sub-data set, the blood vessel depth is calculated by the same method as that for the first sub-data set. In addition, the functions of the information input unit 160 may be incorporated into the console 20.

As described above, as a situation where the oxygen saturation s and the blood vessel thickness φ of the measurement target blood vessel are manually input, a situation where the user already views the oxygen saturation image and the blood vessel thickness measurement image to recognize approximate oxygen saturation and blood vessel thickness before the blood vessel depth is measured. In addition, the blood vessel depth calculation unit 98 may be capable of executing two modes of an automatic mode in which the first sub-data set is narrowed on the basis of the oxygen saturation s* and the blood vessel thickness φ* of the measurement target blood vessel measured by the oxygen saturation measurement unit 64 and the blood vessel thickness measurement unit 66, and a manual mode in which the second sub-data set is narrowed on the basis of the manually input oxygen saturation s and blood vessel thickness φ of the measurement target blood vessel. In this case, any mode of the automatic mode and the manual mode may be selectively set by the operating member, such as the console 20.

In addition, in the above embodiment, the blood vessel contrast is used to calculate the blood vessel depth. However, other blood vessel index values may be used. The blood vessel index values include, for example, the brightness value (average value or the like) of the measurement target blood vessel and the color information of the measurement target blood vessel. As the color information, there are calculated values obtained by the calculation based on the R2 image signal, the G2 image signal, and the B2 image signal, for example, signal ratios, such as R2/G2 and B2/G2, the color difference signals Cr and Cb, saturation S, hue H, and the like. Additionally, the blood vessel index values may be a value obtained by combining the blood vessel contrast, the brightness value of a blood vessel part, and the color information of the blood vessel part together.

In addition, in the above embodiment, the blood vessel depth is calculated by measuring the oxygen saturation and the blood vessel depth other than the blood vessel depth after the relationship between the blood vessel contrast, and the oxygen saturation, the blood vessel thickness, and the blood vessel depth are determined and by using the measurement results and the relationship. However, the invention is not limited to this. The blood vessel depth may be calculated by measuring a specific blood vessel index value variation factor other than the blood vessel depth that varies blood vessel index values after the blood vessel index values, such as the blood vessel contrast, and a relationship between the specific blood vessel index value variation factor and the blood vessel depth are determined in advance and by using the measurement results and the relationship.

Figure 20:
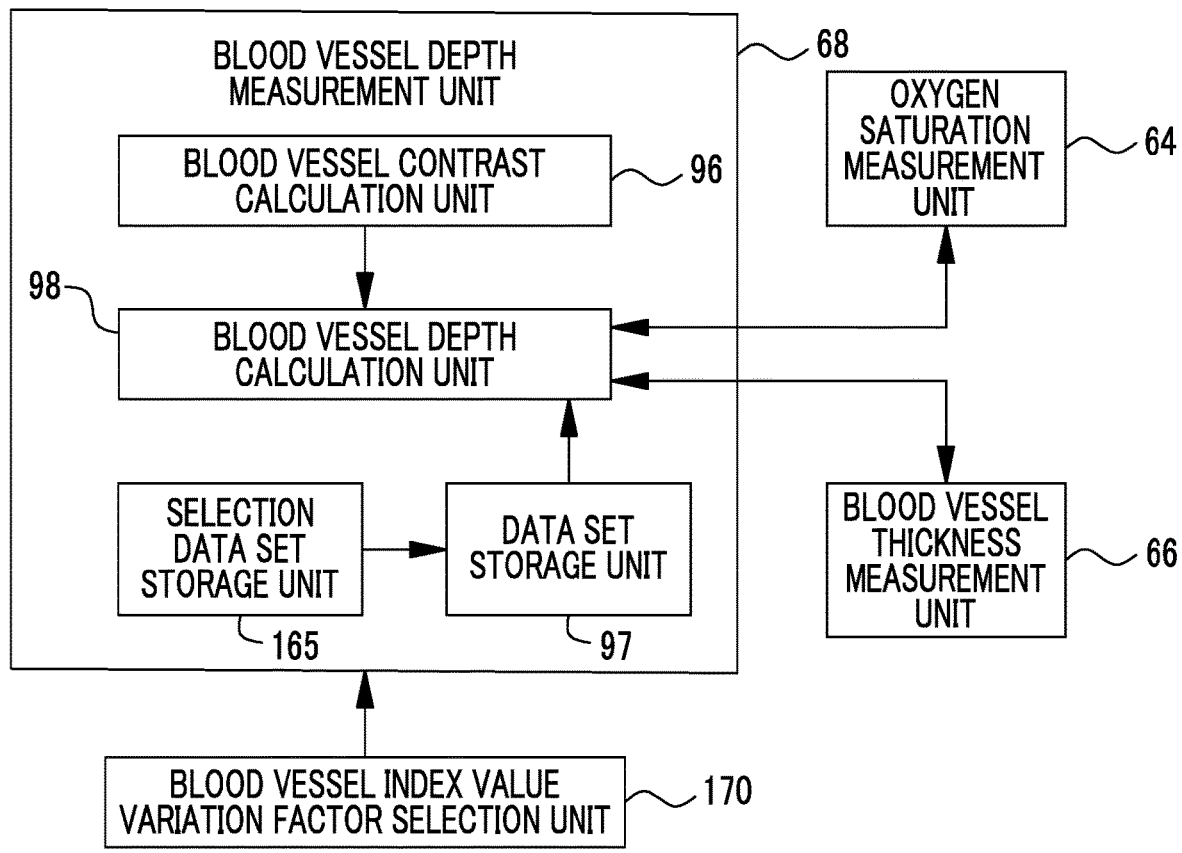
FIG. 20 is a block diagram illustrating the functions of a blood vessel depth measurement unit to which a blood vessel index value variation factor selection unit is connected.

In this case, in order to be capable of selecting or adding a specific blood vessel index value variation factor among a plurality of blood vessel index value variation factors, as illustrated in FIG. 20, it is preferable to store selection data set constituted with measurement data, in which the respective blood vessel index value variation factors are associated with the blood vessel index values, in advance in a selection data set storage unit 165. In a case where the specific blood vessel index value variation factor is selected by a blood vessel index value variation factor selection unit 170 connected to the blood vessel depth measurement unit 68, a selection data set corresponding to the selected blood vessel index value variation factor is read from the selection data set storage unit 165 and is integrated as one data set. This integrated data set is stored in the data set storage unit 97, and the blood vessel depth is calculated by the same method. In addition, in a case where the specific blood vessel index value variation factor other than the oxygen saturation and the blood vessel thickness is selected, a specific measurement unit that can measure the specific blood vessel index value variation factor is newly required.

In addition, in a case where there are a plurality of specific blood vessel index value variation factors, it is preferable to fix some factors to a representative value (for example, "70%" in the case of the oxygen saturation) and to use a data set in which the blood vessel index values and the blood vessel depth are associated with each other regarding the other specific blood vessel index value variation factors. In this case, measurement or input of some specific blood vessel index value variation factors that are fixed to the representative value is not performed, and only measurement or input of the other specific blood vessel index value variation factors is performed.

As the specific blood vessel index value variation factors, there are the following factors in addition to the oxygen saturation and the blood vessel thickness. For example, since an imaging distance and an imaging angle are specific blood vessel index value variation factors that vary the blood vessel contrast, the blood vessel depth may be calculated from a relationship between the blood vessel contrast, the imaging distance or the imaging angle, and the blood vessel depth. For example, since blood vessel density is also a specific blood vessel index value variation factor that varies the blood vessel contrast, the blood vessel depth may be calculated from a relationship between the blood vessel contrast, the blood vessel density, and the blood vessel depth. As other specific blood vessel index value variation factors, there are the density of a yellow coloring agent, such as bilirubin, the scattering coefficient of a mucous membrane, and the like. In addition, it is preferable that imaging distance is calculated from the average brightness of a whole mucous membrane.

Additionally, it is preferable that the imaging angle is estimated from the brightness distribution of a whole image. Additionally, it is preferable that a blood vessel region in an image is extracted and the blood vessel density is calculated on the basis of the extracted blood vessel region.

Second Embodiment

Figure 21:
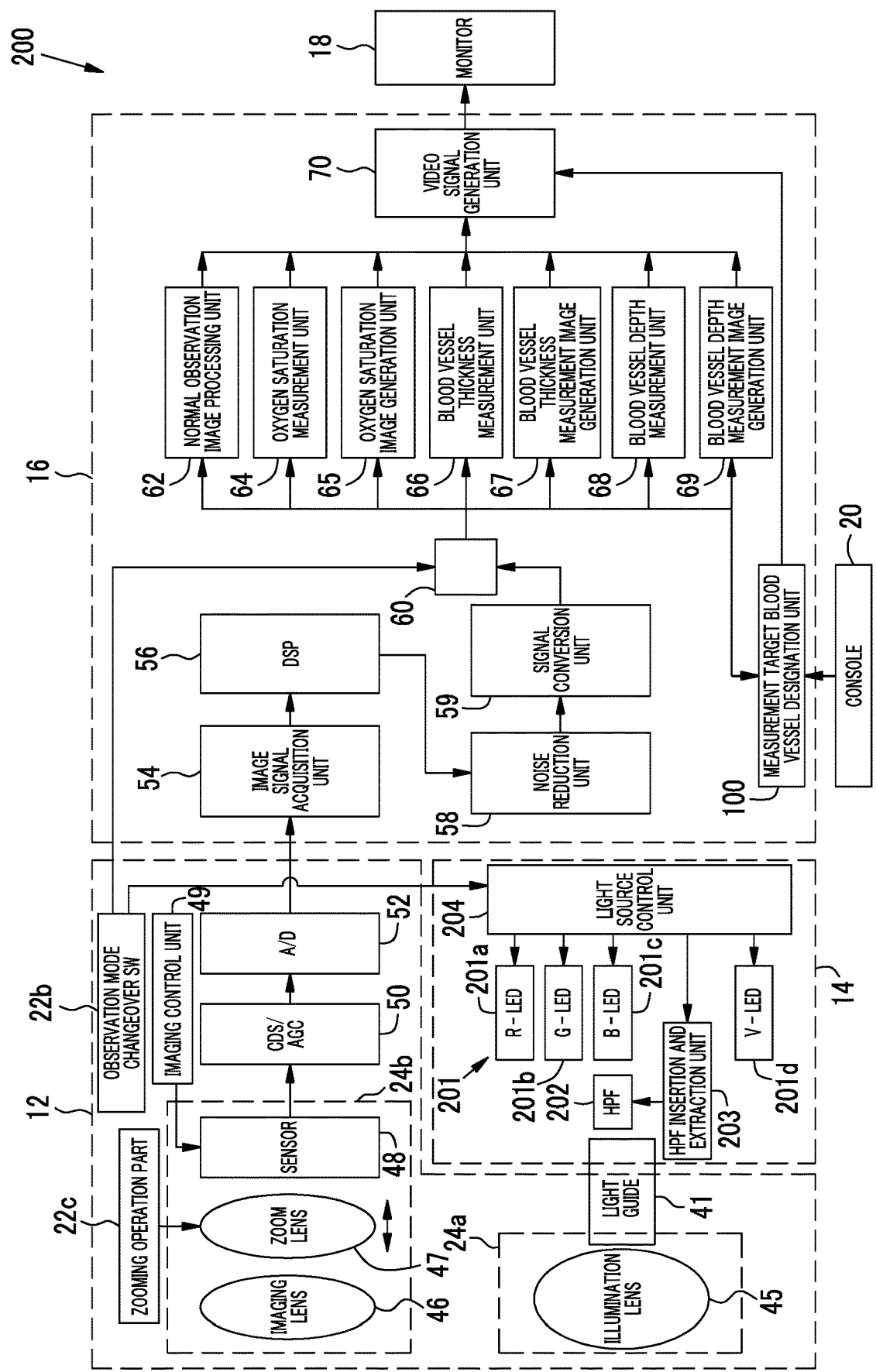
FIG. 21 is a block diagram of an endoscopic system of a second embodiment.

As illustrated in FIG. 21, the light source device 14 of an endoscopic system 200 is provided with a light emitting diode (LED) light source unit 201 and an LED light source control unit 204 instead of the first and second blue laser light sources 34 and 36 and the violet laser light source 38, and the light source control unit 40. Additionally, the illumination optical system 24a of the endoscopic system 200 is not provided with the fluorescent body 44. The others are the same as those of the endoscopic system 10 of the first embodiment.

Figure 22:
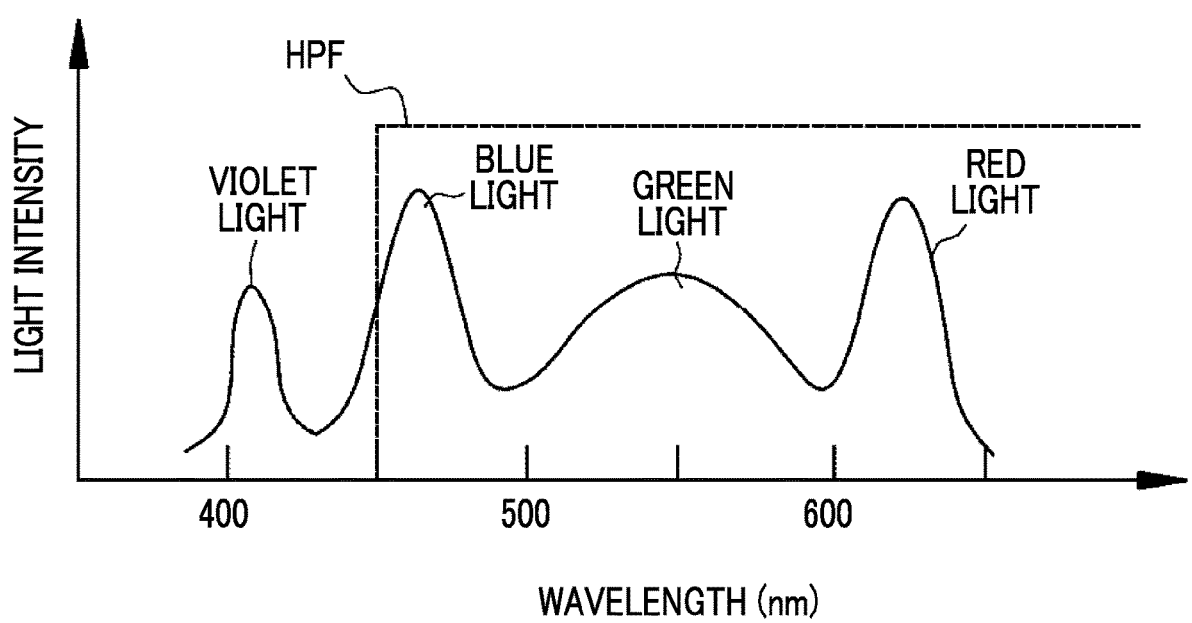
FIG. 22 is a graph illustrating a light emission band of a light emitting diode (LED), and the characteristics of a high-pass filter (HPF).

The LED light source unit 201 has an R-LED 201a, a G-LED 201b, a B-LED 201c, and a V-LED 201d as light sources that emit light limited to specific wavelength ranges. As illustrated in FIG. 22, the R-LED 201a emits, for example, red range light (hereinafter simply referred to as red light) of about 600 to 650 nm. The central wavelength of this red light is about 620 to 630 nm. The G-LED 201b emits green range light (hereinafter simply referred to as green light) of about 500 to 600 nm expressed by a normal distribution. The B-LED 201c emits blue range light (hereinafter simply referred to as blue light) having 445 to 460 nm as its central wavelength. The V-LED 201d emits violet range light (hereinafter simply referred to as violet light) having 400 to 410 nm as its central wavelength.

Additionally, the LED light source unit 201 has a high-pass filter (HPF) 202 that is inserted into and extracted from an optical path of blue light emitted by the B-LED 201c. The high-pass filter 202 cuts blue light in a wavelength range of about 450 nm or less. Since the blue light of which the wavelength range of about 450 nm or less is cut consists of a wavelength range (refer to FIG. 8) with a larger light absorption coefficient of the oxygenated hemoglobin than the light absorption coefficient of the reduced hemoglobin, the blue light can be used for measurement of the oxygen saturation. For that reason, hereinafter, the blue light of which the wavelength range of about 450 nm or less is cut is referred to as blue light for measurement. In addition, the insertion and extraction of the high-pass filter 202 is performed by an HPF insertion and extraction unit 203 under the control of the LED light source control unit 204.

The LED light source control unit 204 controls ON/OFF and respective light emission amounts of the LEDs 201a to 201d of the LED light source unit 201 and the insertion and extraction of the high-pass filter 202. Specifically, in the case of the normal observation mode and the blood vessel thickness measurement mode, the LED light source control unit 204 turns on all the respective LEDs 201a to 201d and the high-pass filter 202 retracts the B-LED 301c from the optical path. Accordingly, the white light in which the violet light, the blue light, the green light, and the red light overlap each other is radiated to the observation target, and the sensor 48 images the observation target with reflected light of the white light, and outputs the Bc image signal, the Gc image signal, and the Rc image signal.

On the other hand, in the case of the oxygen saturation mode and the blood vessel depth measurement mode, the LED light source control unit 204 performs the control of alternately switching ON of only the B-LED 203d and ON of all the LED 203a to 203d in each frame, in a state where the high-pass filter 202 is inserted. Accordingly, the blue light for measurement, and mixed light including the violet light, and the blue light for measurement, the green light, and the red light are alternately radiated to the observation target.

Also, the imaging control unit 49 images signal charges obtained by imaging the observation target under the blue light for measurement in the reading period of the first frame and outputs the B1 image signal, the G1 image signal, and the R1 image signal. Additionally, signal charges obtained by imaging the observation target under the mixed light including the violet light, the blue light for measurement, the green light, and the red light are read in the reading period of the second frame, and the B2 image signal, the G2 image signal, and the R2 image signal are output. The subsequent processing can be performed similarly to the endoscopic system 10.

Third Embodiment

Figure 23:
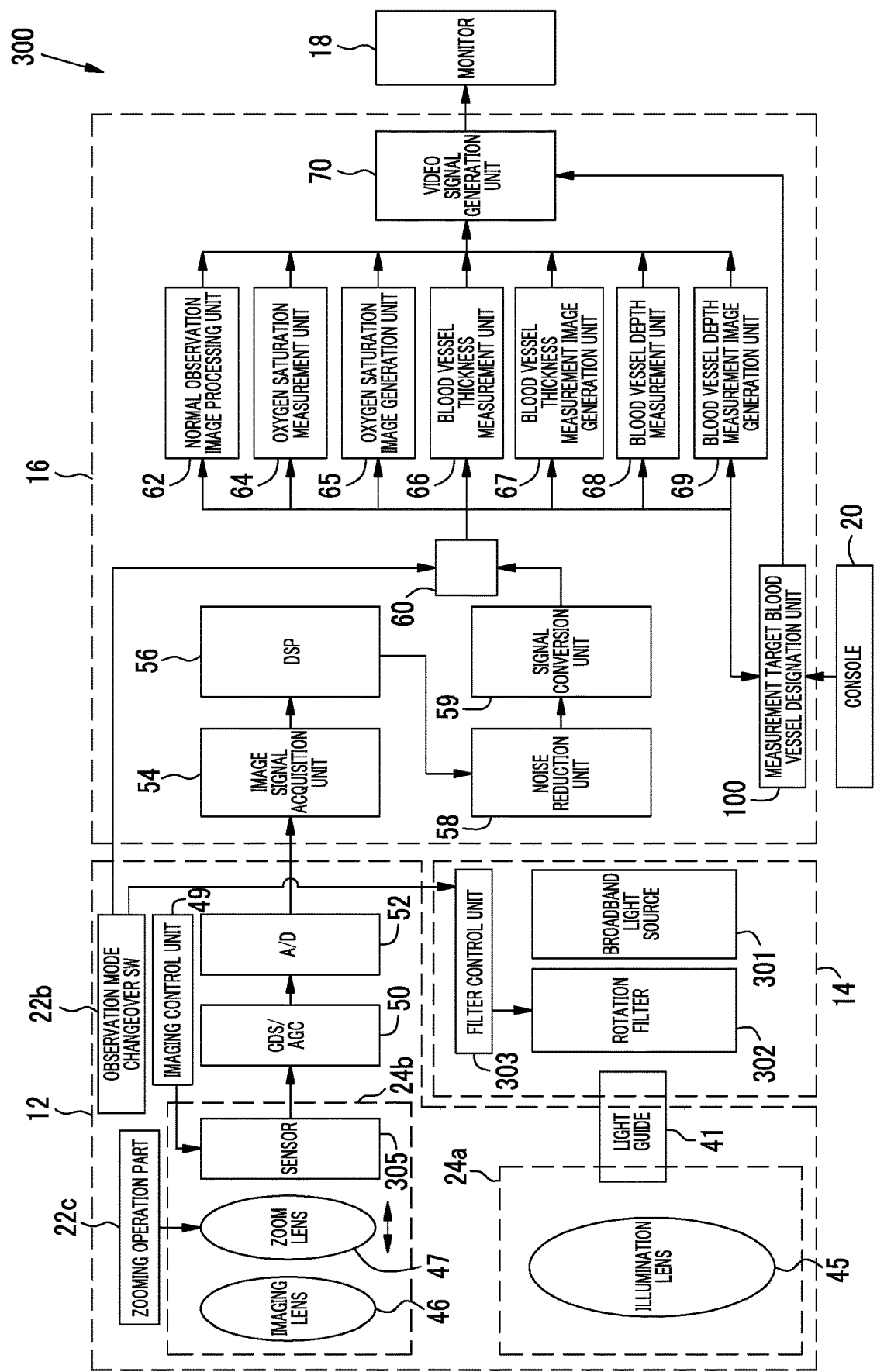
FIG. 23 is a block diagram of an endoscopic system of a third embodiment.

As illustrated in FIG. 23, the light source device 14 of an endoscopic system 300 is provided with a broadband light source 301, a rotation filter 302, and a rotation filter control unit 303 instead of the first and second blue laser light sources 34 and 36 and the violet laser light source 38, and the light source control unit 40. Additionally, a sensor 305 of the endoscopic system 300 is a monochrome image pickup element that is not provided with a color filter. For this reason, the DSP 56 does not perform processing, such as the demosaicing processing, which is unique to the color image pickup element. The others are the same as those of the endoscopic system 10 of the first embodiment.

The broadband light source 301 includes, for example, a xenon lamp, a white LED, or the like, and emits white light of which the wavelength range ranges from blue to red. The rotation filter 302 includes a first filter 310 and a second filter 311 (refer to FIG. 24), and is movable in a radial direction between a first position where the first filter 310 is disposed and a second position where the second filter 311 is disposed, on an optical path where the white light emitted from the broadband light source 301 enters the light guide 41.

The mutual movement of the rotation filter 302 to the first position and the second position is controlled by the rotation filter control unit 303 in accordance with a selected observation mode. Additionally, the rotation filter 302 rotates in accordance with the imaging frame of the sensor 305 in a state where the rotation filter 302 is disposed at the first position or the second position. The rotating speed of the rotation filter 302 is controlled by the rotation filter control unit 303 in accordance with the selected observation mode.

Figure 24:
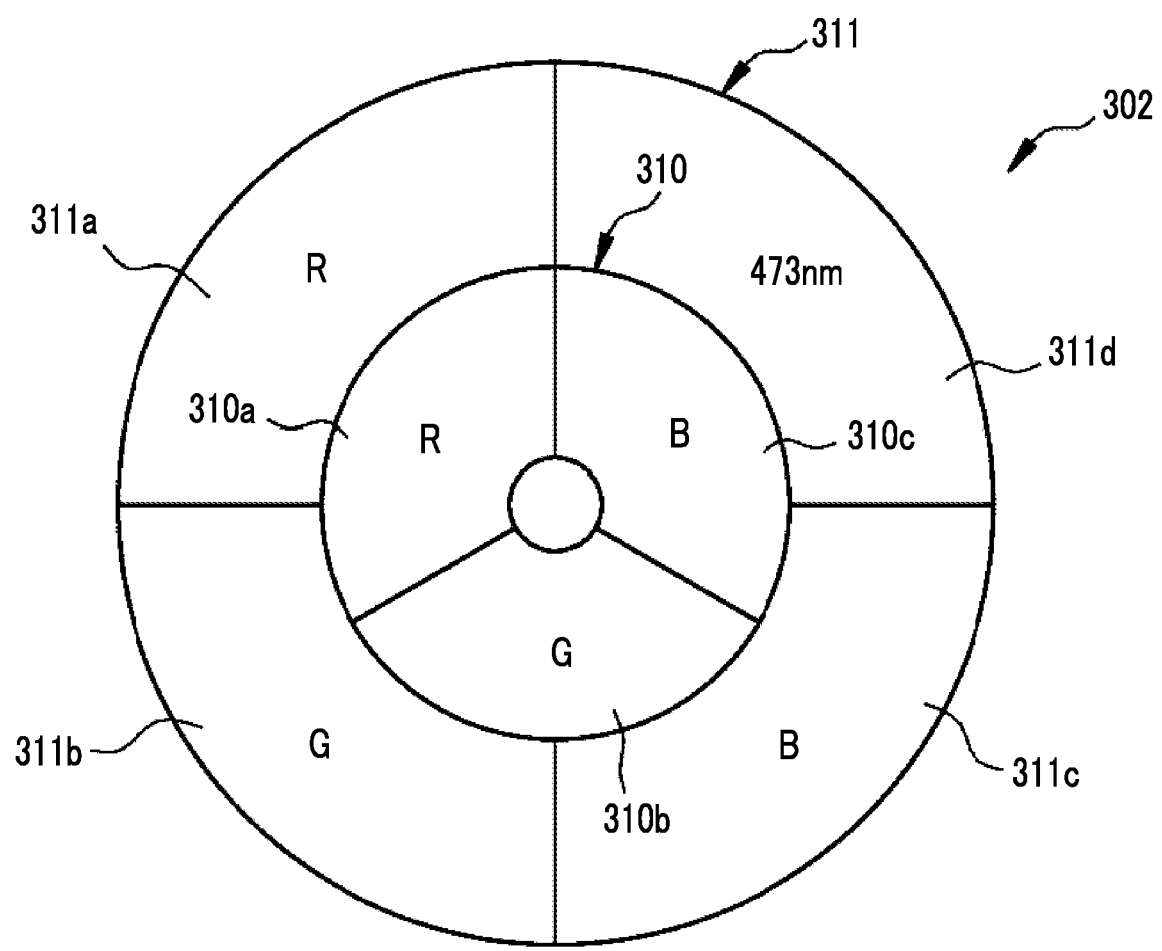
FIG. 24 is a plan view of a rotation filter.
Figure 25:
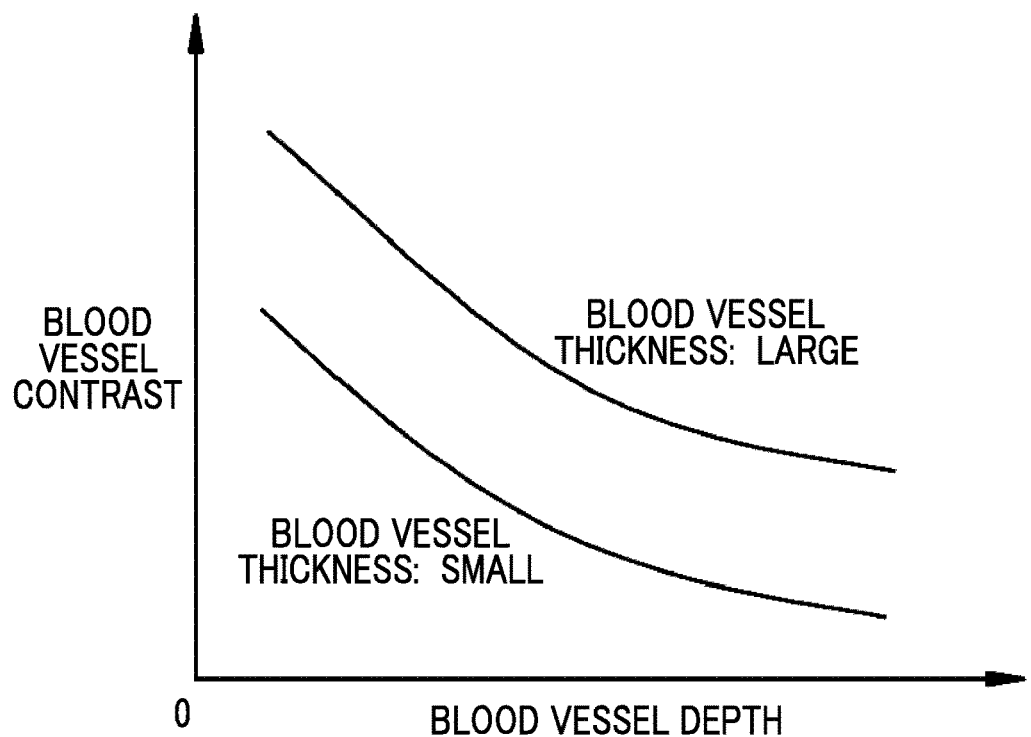
FIG. 25 is a graph illustrating a relationship between the blood vessel depth and the blood vessel contrast in a case where the blood vessel thickness varies.
Figure 26:
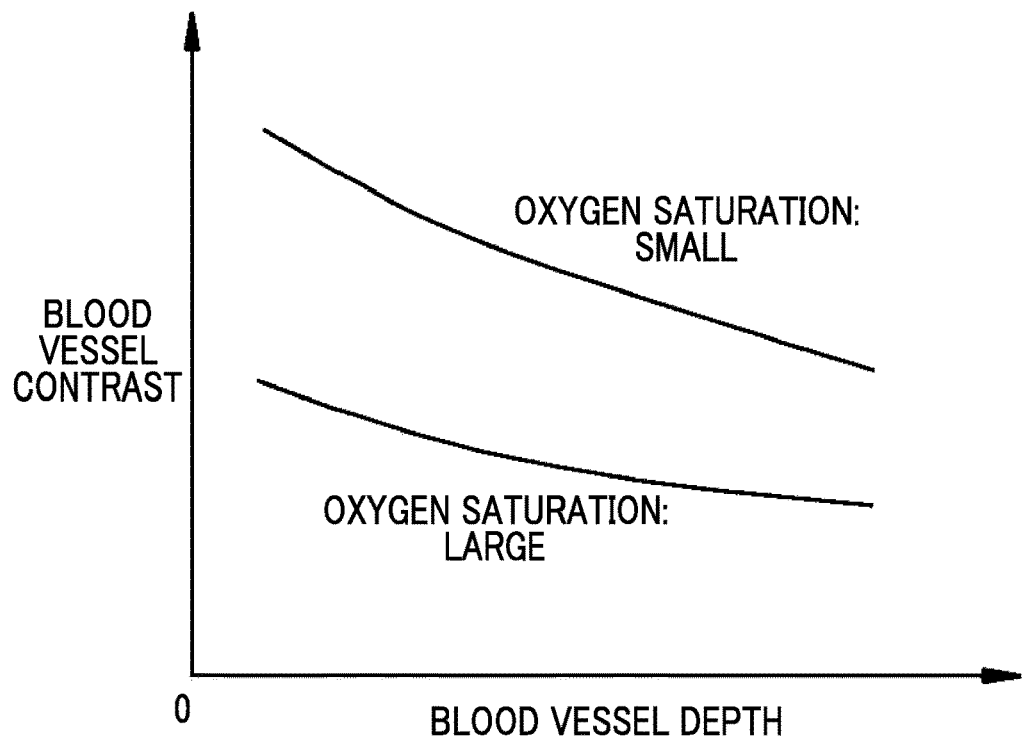
FIG. 26 is a graph illustrating a relationship between the blood vessel depth and the blood vessel contrast in a case where the oxygen saturation varies.

As illustrated in FIG. 24, the first filter 310 is used in the normal observation mode and the blood vessel thickness measurement mode and is provided at an inner peripheral part of the rotation filter 302. The first filter 310 has an R filter 310a that transmits the red light, a G filter 310b that transmits the green light, and a B filter 310c that transmits blue violet light including the violet light and the blue light. In a case where the normal observation mode and the blood vessel thickness measurement mode are set, the rotation filter 302 is disposed at the first position, and the white light from the broadband light source 301 enters any of the R filter 310a, the G filter 310b, and the B filter 310c in accordance with the rotation of the rotation filter 302. For this reason, the red light, the green light, and the blue violet light are sequentially radiated to the observation target in accordance with filters that these lights have transmitted. The sensor 305 sequentially outputs the Rc image signal, the Gc image signal, and the Bc image signal by imaging the observation target with reflected lights of those lights, respectively.

Additionally, the second filter 311 is used in the oxygen saturation mode and the blood vessel depth measurement mode and is provided at an outer peripheral part of the rotation filter 302. The second filter 311 has an R filter 311a that transmits the red light, a G filter 311b that transmits the green light, a B filter 311c that transmits blue violet light including the violet light and the blue light, and a narrowband filter 311d that transmit narrowband light of 473±10 nm. In a case where the oxygen saturation mode and the blood vessel depth measurement mode are set, the rotation filter 302 is disposed at the second position, and the white light from the broadband light source 301 enters any of the R filter 311a, the G filter 311b, the B filter 311c, and the narrowband filter 311d in accordance with the rotation of the rotation filter 302. For this reason, the red light, the green light, the blue violet light, and the narrowband light (473 nm) are sequentially radiated to the observation target in accordance with filters that these lights have transmitted.

The sensor 405 images the observation target to output the R2 image signal in a case where the red light is radiated, images the observation target to output the G2 image signal in a case where the green light is radiated, images the observation target to output the B2 image signal in a case where the blue violet light is radiated, and images the observation target to output the B1 image signal in a case where the narrowband light is radiated. The subsequent processing can be performed similarly to the endoscopic system 10 of the first embodiment.

The oxygen saturation is calculated in the first to third embodiments. However, instead of this or in addition to this, other biological function information, such as an oxygenated hemoglobin index found from "Amount of blood×Oxygen saturation (%)" and a reduced hemoglobin index found from "Amount of blood×(1−Oxygen saturation)(%)" may be calculated.

EXPLANATION OF REFERENCES

- 10: endoscopic system
- 12: endoscope
- 14: light source device
- 16: processor device
- 17: universal cord
- 18: monitor
- 20: console
- 21: insertion part
- 22: operating part
- 22a: angle knob
- 22c: zooming operation part
- 23: bending part
- 24: distal end part
- 24a: illumination optical system
- 24b: imaging optical system
- 34: first blue laser light source
- 36: second blue laser light source
- 38: violet laser light source
- 40: light source control unit
- 41: light guide
- 44: fluorescent body
- 45: illumination lens
- 46: imaging lens
- 47: zoom lens
- 48: sensor
- 49: imaging control unit
- 50: CDS/AGC circuit
- 52: A/D converter
- 54: image signal acquisition unit
- 56: DSP
- 58: noise reduction unit
- 59: signal conversion unit
- 60: image processing switching unit
- 62: normal observation image processing unit
- 64: oxygen saturation measurement unit
- 65: oxygen saturation image generation unit
- 66: blood vessel thickness measurement unit
- 67: blood vessel thickness measurement image generation unit
- 68: blood vessel depth measurement unit
- 69: blood vessel depth measurement image generation unit
- 70: video signal generation unit
- 81: signal ratio calculation unit
- 82: correlation storage unit
- 83: oxygen saturation calculation unit
- 90: graph
- 91: graph
- 93: lower limit line
- 94: upper limit line
- 96: blood vessel contrast calculation unit
- 97: data set storage unit
- 98: blood vessel depth calculation unit
- 100: measurement target blood vessel designation unit
- 102: blood vessel selection image
- 104: selection pointer
- 110: blood vessel thickness measurement image
- 120: data set
- 150: blood vessel depth measurement image
- 160: information input unit
- 170: blood vessel index value variation factor selection unit
- 200: endoscopic system
- 201: LED light source unit
- 202: high-pass filter
- 203: insertion and extraction unit
- 204: light source control unit
- 300: endoscopic system
- 301: broadband light source
- 302: rotation filter
- 303: rotation filter control unit
- 305: sensor
- 310: first filter
- 310a: R filter
- 310b: G filter
- 310c: B filter
- 311: second filter
- 311a: R filter
- 311b: G filter
- 311c: B filter
- 311d: narrowband filter
- 405: sensor

What is claimed is:

1. An image processing device that measures a blood vessel depth of a blood vessel in an observation target, the image processing device comprising:
a memory storing a data set including a plurality of blood vessel index value variation factors and a plurality of blood vessel index values respectively associated with the plurality of blood vessel index value variation factors, wherein the plurality of blood vessel index value variation factors include the blood vessel depth; and
a processor, configured to:
acquire an image obtained by imaging the observation target;
calculate a blood vessel index value from a blood vessel index value image in the acquired image, wherein the blood vessels index value image comprises multiple-wavelength images;
select a specific blood vessel index value variation factor other than the blood vessel depth among the plurality of blood vessel index value variation factors in the acquired image; and select a sub-data set having the specific blood vessel index value variation factor from the data set and obtain a blood vessel depth corresponding to the blood vessel index value according to the sub-data set.

2. The image processing device according to claim 1, wherein the processor is further configured to:
designate a measurement target blood vessel to be a measurement target for the blood vessel depth in the observation target; and
calculate the blood vessel index value of the measurement target blood vessel.

3. The image processing device according to claim 2, wherein the processor calculates the blood vessel index value of the measurement target blood vessel on the basis of the multiple-wavelength images.

4. The image processing device according to claim 3, wherein the processor calculates the blood vessel index value for each of the multiple-wavelength images, and calculates the blood vessel index value of the measurement target blood vessel by weighting the calculated blood vessel index values respectively and adding the calculated blood vessel index values to each other, and wherein weighting coefficients of the blood vessel index values are set on the basis of wavelength components of the images used for the calculation of the blood vessel index values.

5. The image processing device according to claim 1, wherein the processor is further configured to:
generate a blood vessel depth measurement image for displaying a calculation result of the blood vessel depth on a display unit.

6. The image processing device according to claim 2, wherein the processor is further configured to:
generate a blood vessel depth measurement image for displaying a calculation result of the blood vessel depth on a display unit.

7. The image processing device according to claim 3, wherein the processor is further configured to:
generate a blood vessel depth measurement image for displaying a calculation result of the blood vessel depth on a display unit.

8. The image processing device according to claim 4, wherein the processor is further configured to:
generate a blood vessel depth measurement image for displaying a calculation result of the blood vessel depth on a display unit.

9. The image processing device according to claim 1, wherein the blood vessel index value is a value obtained by combining at least two or more of a blood vessel contrast, a brightness value of a blood vessel part, or color information of the blood vessel part together.

10. The image processing device according to claim 1, wherein the blood vessel index value variation factors are values obtained by combining two or more of a blood vessel thickness, an oxygen saturation, a blood vessel density, an imaging distance, an imaging angle, a yellow coloring agent density, or a scattering coefficient of a mucous membrane together.

11. The image processing device according to claim 1, wherein the specific blood vessel index value variation factors are a blood vessel thickness and an oxygen saturation, and
wherein the processor is further configured to measure the blood vessel thickness and the oxygen saturation.

12. An image processing device that measures a blood vessel depth of a blood vessel in an observation target, the image processing device comprising:
a memory storing a data set including a plurality of blood vessel index value variation factors and a plurality of blood vessel index values respectively associated with the plurality of blood vessel index value variation factors, wherein the plurality of blood vessel index value variation factors include the blood vessel depth; and
a processor, configured to:
acquire an image obtained by imaging the observation target;
calculate a blood vessel index value from a blood vessel index value image in the acquired image, wherein the blood vessel index value image comprises multiple-wavelength images;
select a specific blood vessel index value variation factor other than the blood vessel depth among the plurality of blood vessel index value variation factors in the acquired image;
select a sub-data set having the specific blood vessel index value variation factor from the data set and obtain a blood vessel depth corresponding to the blood vessel index value according to the sub-data set;
designate a measurement target blood vessel to be a measurement target for the blood vessel depth in the observation target; and
generate a blood vessel depth measurement image for displaying a calculation result of the blood vessel depth on a display unit,
wherein the processor calculates the blood vessel index value of the measurement target blood vessel, for each of the multiple-wavelength images, and calculates the blood vessel index value of the measurement target blood vessel by weighting the calculated blood vessel index values respectively and adding the calculated blood vessel index values to each other,
wherein weighting coefficients of the blood vessel index values are set on the basis of wavelength components of the images used for the calculation of the blood vessel index values,
wherein the specific blood vessel index value variation factors are a blood vessel thickness and an oxygen saturation,
wherein the processor is further configured to measure the blood vessel thickness and the oxygen saturation,
wherein the blood vessel index value is a blood vessel contrast, and
wherein the data set storage unit stores a data set including measurement data in which the blood vessel contrast, the oxygen saturation, and the blood vessel depth are associated with each other.

13. The image processing device according to claim 1, wherein the image processing device is an endoscope processor device.

14. A method for operating an image processing device that measures a blood vessel depth of a blood vessel in an observation target, the method comprising:
acquiring an image obtained by imaging the observation target;
calculating a blood vessel index value from a blood vessel index value image in the acquired image;
measuring selecting a specific blood vessel index value variation factor other than the blood vessel depth among a plurality of blood vessel index value variation factors, in the acquired image; and obtaining a data set including a plurality of items of measurement data in which the blood vessel index value and a plurality of blood vessel index value variation factors are associated with each other, selecting a sub-data set having the specific blood vessel index value variation factor from the data set, and calculating a blood vessel depth corresponding to the blood vessel index value.

15. The method for operating the image processing device according to claim 14, wherein the image processing device is an endoscope processor device.

\* \* \* \* \*